US011970528B2

(12) United States Patent
Orentas et al.

(10) Patent No.: US 11,970,528 B2
(45) **Date of Patent: *Apr. 30, 2024**

(54) COMPOSITIONS AND METHODS FOR TREATING CANCER WITH ANTI-MESOTHELIN IMMUNOTHERAPY

(71) Applicants: Lentigen Technology Inc., Gaithersburg, MD (US); The U.S.A., as represented by the Secretary, Department of Health and Human Services, Bethesda, MD (US)

(72) Inventors: Rimas Orentas, Washington, DC (US); Dina Schneider, Potomac, MD (US); Boro Dropulic, Gaithersburg, MD (US); Dimiter S. Dimitrov, Frederick, MD (US); Zhongyu Zhu, Frederick, MD (US)

(73) Assignees: LENTIGEN TECHNOLOGY, INC., Gaithersburg, MD (US); The U.S.A., as represented by the Secretary, Department of Health and Human Services, Bethesda, MD (US)

( * ) Notice: Subject to any disclaimer, the term of this patent is extended or adjusted under 35 U.S.C. 154(b) by 206 days.

This patent is subject to a terminal disclaimer.

(21) Appl. No.: 16/780,325

(22) Filed: Feb. 3, 2020

(65) Prior Publication Data

US 2020/0231663 A1 Jul. 23, 2020

Related U.S. Application Data

(63) Continuation of application No. 16/252,158, filed on Jan. 18, 2019, now Pat. No. 10,550,179, which is a continuation of application No. 15/866,222, filed on Jan. 9, 2018, now Pat. No. 10,183,993.

(60) Provisional application No. 62/444,201, filed on Jan. 9, 2017.

(51) Int. Cl.

| | |
|---|---|
| ***C07K 16/18*** | (2006.01) |
| ***A61K 35/17*** | (2015.01) |
| ***A61P 35/00*** | (2006.01) |
| ***A61P 35/02*** | (2006.01) |
| ***C07K 14/705*** | (2006.01) |
| ***C07K 14/725*** | (2006.01) |
| ***C07K 16/30*** | (2006.01) |
| ***C12N 5/0783*** | (2010.01) |
| ***C12N 15/07*** | (2006.01) |
| ***C12N 15/09*** | (2006.01) |
| ***C12N 15/10*** | (2006.01) |
| ***C12N 15/62*** | (2006.01) |
| ***C12N 15/63*** | (2006.01) |

(52) U.S. Cl.

CPC .............. *C07K 16/18* (2013.01); *A61K 35/17* (2013.01); *A61P 35/00* (2018.01); *A61P 35/02* (2018.01); *C07K 14/7051* (2013.01); *C07K 14/70517* (2013.01); *C07K 14/70521* (2013.01); *C07K 14/70578* (2013.01); *C07K 16/30* (2013.01); *C12N 5/0636* (2013.01); *C12N 5/0638* (2013.01); *C12N 15/09* (2013.01); *C12N 15/10* (2013.01); *C12N 15/62* (2013.01); *C12N 15/63* (2013.01); *C07K 2317/21* (2013.01); *C07K 2317/622* (2013.01); *C07K 2319/02* (2013.01); *C07K 2319/03* (2013.01); *C07K 2319/33* (2013.01)

(58) Field of Classification Search

CPC .... A61K 35/17; C12N 5/0636; C12N 5/0638; C12N 15/62; C12N 15/63; C07K 16/18; C07K 16/30; C07K 2317/622; C07K 14/70517; C07K 14/70521; C07K 2319/03

See application file for complete search history.

(56) References Cited

U.S. PATENT DOCUMENTS

| | | | | |
|---|---|---|---|---|
| 2005/0069542 | A1 | 3/2005 | Baker et al. | |
| 2007/0266449 | A1* | 11/2007 | Zivin ................ | C12N 15/8509 800/9 |
| 2015/0031624 | A1 | 1/2015 | Feldman | |
| 2015/0139943 | A1 | 5/2015 | Campana et al. | |

FOREIGN PATENT DOCUMENTS

| | | | |
|---|---|---|---|
| CN | 101977932 | A | 2/2011 |
| CN | 103946242 | A | 7/2014 |
| CN | 104780393 | A | 7/2015 |
| EP | 1497445 | | 1/2005 |
| WO | WO 2013063419 | | 5/2013 |
| WO | WO 2015090230 | | 6/2015 |
| WO | WO 2015188141 | | 12/2015 |
| WO | WO 2015188142 | | 12/2015 |

(Continued)

OTHER PUBLICATIONS

Martin et al., BioTechniques, 2019, 66(4): 167-170.*

(Continued)

*Primary Examiner* — Hong Sang

(74) *Attorney, Agent, or Firm* — Serge Sira; Gregory Hwa, Esq; Fish & Richardson P.C.

(57) ABSTRACT

Chimeric antigen receptors containing mesothelin antigen binding domains are disclosed. Nucleic acids, recombinant expression vectors, host cells, antigen binding fragments, and pharmaceutical compositions, relating to the chimeric antigen receptors are also disclosed. Methods of treating or preventing cancer in a subject, and methods of making chimeric antigen receptor T cells are also disclosed.

18 Claims, 7 Drawing Sheets

Specification includes a Sequence Listing.

(56) References Cited

FOREIGN PATENT DOCUMENTS

| | | |
|---|---|---|
| WO | WO 2016164731 | 10/2016 |
| WO | WO 2016/179319 | 11/2016 |

OTHER PUBLICATIONS

Fu et al., Oncology Letters, 2020, 20:36: 1-9.*
EP Extended Search Report in European Application. No. 21160649.6, dated Aug. 6, 2021, 6 pages.
Bendig, "Humanization of rodent monoclonal antibodies by CDR grafting," Methods: A Companion to Methods in Enzymology, 1995, 8:83-93.
Brown, et al., "Stem-like tumor-initiating cells isolated from IL12Rα2 expressing gliomas are targeted and killed by IL13-zetakine-redirected T cells," Clin. Cancer Res., 2012, 18(8):2199-2209.
Carpenito, et al., "Control of large, established tumor xenografts with genetically retargeted human T cells containing CD28 and CD137 domains," Proc. Natl. Acad. Sci. USA, 2009, 106:3360-3365.
Chang, et al..,"Isolation and Characterization of a Monoclonal Antibody, K1, Reactive with Ovarian Cancers and Normal Mesothelium," Int. J. Cancer, 1992, 50:373-81.
Cheng, et al., "High mesothelin correlates with chemoresistance and poor survival in epithelial ovarian carcinoma," Br. J. Cancer, 2009, 100:1144-1153.
Chowdhury, et al., "Improving antibody affinity by mimicking somatic hypermutation in vitro," Nat. Biotech., 1999, 17:568-72.
Chowdhury, et al., "Isolation of a high-affinity stable single-chain Fv specific for mesothelin from DNA-immunized mice by phage display and construction of a recombinant immunotoxin with anti-tumor activity," Proc. Natl. Acad. Sci. USA, 1998, 95:669-74.
Colman, "Effects of amino acid sequence changes on antibody-antigen interactions," Research in Immunology, 1994, 145:33-36.
Di Stasi, et al., "Inducible Apoptosis as a Safety Switch for Adoptive Cell Therapy," N. Engl. J. Med., 2011, 365(18):1673-83.
Foster et al., "Antitumor Activity of EBV-specific T Lymphocytes Transduced with a Dominant Negative TGF-B Receptor," J. Immunother., 2008, 31(5):500-505.
Haso et al., "Anti-CD22-chimeric antigen receptors targeting B cell precursor acute lymphoblastic leukemia," Blood, 2012, 121(7):1165-74.
Hassan and Ho, "Mesothelin targeted cancer immunotherapy," Eur. J. Cancer, 2008, 44(1):46-53.
Hassan, et al., "Mesothelin is overexpressed in pancreaticobiliary adenocarcinomas but not in normal pancreas and chronic pancreatitis," Am. J. Clin. Pathol., 2005, 124:838-45.
Hegde, et al., "Combinational targeting offsets antigen escape and enhances effector functions of adoptively transferred T cells in glioblastoma," Mol. Ther., 2013, 21(11):2087-2101.
Houdebine, "Production of pharmaceutical proteins from transgenic animals," J. Biotech., 1994, 34:269-87.
International Search Report and Written Opinion, issued in PCT/US2018/012954, dated May 14, 2018, 9 pages.
Kaneko, et al., "A binding domain on mesothelin for CA125/MUC16," J. Biol. Chem., 2009, 284:3739-3749.
Kappell, et al., "Regulating gene expression in transgenic animals," Current Opinions in Biotechnology, 1992, 3:548-53.
Khantasup, et al., "Design and generation of humanized single-chain Fv derived from mouse mybridoma for potential targeting application," Monoclonal Antibodies in Immunodiagnosis and Immunotherapy, 2015, 34(6):404-417.
Kloss, et al., "Combinatorial antigen recognition with balanced signaling promotes selective tumor eradication by engineered T cells," Nat. Biotechnol., 2013, 31(1):71-75.
Kochenderfer, et al., "B-cell depletion and remissions of malignancy along with cytokine-associated toxicity in a clinical trial of anti-CD19 chimeric-antigen-receptor-transduced T cells," Blood, 2012, 119(12):2709-20.
Lanitis, et al., "Chimeric antigen receptor T cells with dissociated signaling domains exhibit focused anti-tumor activity with reduced potential for toxicity in vivo," Cancer Immunol. Res., 2013, 1(1):43-53.
Lee, et al., "Anti-CD19 Chimeric Antigen (CAR) T Cells Produce Complete Responses with Acceptable Toxicity But Without Chronic B-Cell Aplasia in children with Relapsed or Refractory Acute Lymphoblastic Leukemia (All) Even After Allogeneic Hematopoietic Stem Cell Transplantation (HSCT)," American Society of Hematology Annual Meeting, New Orleans, LA; Dec. 7-10, 2013.
Lehner et al., "Redirecting T cells to Ewing's sarcoma family of tumors by a chimeric NKG2D receptor expressed by lentiviral transduction or mRNA transfection," PLoS One, 7 (2): e31210, 2012.
Long et al., "Lessons learned from a highly-active CD22-specific chimeric antigen receptor," Oncoimmunology, 2013, 2(4):e23621.
Newick et al., "Chimeric antigen receptor T-cell therapy for solid tumors," Molecular Therapy-Oncolytics, 2016, 3:16006, 7 pages.
Ordonez, "Application of mesothelin immunostaining in tumor diagnosis," Am. J. Surg. Pathol., 1993, 27:1418-28.
Overbeek, "Factors affecting transgenic animal production," Transgenic Animal Technology, Pinkert, ed., 1994, pp. 96-98.
Paul, Fundamental Immunology, 3rd Ed., 1993, Chapter 9, "Structure and Function of Immunoglobulins," pp. 292-295.
Porter, et al., "Chimeric Antigen Receptor-Modified T Cells in Chronic Lymphoid Leukemia," N. Engl. J. Med., 2011, 365(8):725-33.
Rudikoff, et al., "Single amino acid substitution altering antigen-binding specificity," PNAS USA, 1982, 79(6):1979-1983.
Rump, et al., "Binding of ovarian cancer antigen CA125/MUC16 to mesothelin mediates cell adhesion," J. Biol. Chem., 2004, 279:9190-9198.
Tchou, et al., "Mesothelin, a novel immunotherapy target for triple negative breast cancer," Breast Cancer Res. Treat., 2012, 133:799-804.
Wall, "Transgenic Livestock: Progress and Prospects for the Future," Theriogenology, 1996, 45:57-68.
Yvon, et al., "Immunotherapy of mestastatic melanoma using genetically engineered GD2-specific T cells," Clin. Cancer Res., 2009, 15(18): 5852-60.
Zhao et al., "A Herceptin-based chimeric antigen receptor with modified signaling domains leads to enhanced survival of transduced T lymphocytes and antitumor activity," J. Immunol., 2009, 183(9):5563-74.
PCT International Preliminary Report on Patentability in International Application. No. PCT/US2018/012954, dated Jul. 9, 2019, 7 pages.
Chen et al., "Preparation and characterization of the monoclonal antibody against human soluble mesothelin-related proteins," Chinese Journal of Cellular and Molecular Immunology, Mar. 1, 2007, 23(3):246-8.
Office Action in Chinese Appln. No. 201880015253.2, dated Nov. 14, 2022, 16 pages (with English translation).
Office Action in Australian Patent Application No. 2022204182, dated May 1, 2023, 5 pages.
Extended Search Report in European Application No. 22204578.3, dated Apr. 3, 2023, 6 pages.

* cited by examiner

CAR T Diagram pLTG1901 EF1a MH1P--CD8TM-4-1BB-CD3 zeta nucleic acid sequence

ATGCTGCTGCTGGTGACCAGCCTGCTGCTGTGCGAACTGCCGCATCCGGCGTTTCTGCT
GATTCCGCAGGTACAGCTGCAGCAGTCAGGTCCAGGACTGGTGAAGCCCTCGCGGACC
CTCTCACTCACCTGTGCCATCTCCGGGGACAGTGTCTCTAGCAACAGTGCTGCTTGGAA
CTGGATCAGGCAGTCCCCATCGAGAGGCCTTGAGTGGCTGGGAAGGACATACTACAGG
TCCAAGTGGTATAATGATTATGCAGTATCTGTGAAAAGTCGAATAACCATCAACCCAGAC
ACATCCAAGAACCAGTTCTCCCTGCAGCTGAACTCTGTGACTCCCGAGGACACGGCTGT
GTATTACTGTGCAAGAGGGAAGGGTGGTAAGAAGGGTGGTGCTTTTGATATCTGGGGCC
AAGGGACAATGGTCACCGTCTCTTCAGGAGGTGGCGGGTCTGGTGGAGGCGGTAGCG
GCGGTGGCGGATCCTCTTCTGAGCTGACTCAGGACCCTGCTGTGTCTGTGGCCTTGGG
ACAGACAGTCAGGATCACATGCCAAGGAGACAGCCTCAGAAGCTATTATGCAAGCTGGT
ACCAGCAGAAGCCAGGACAGGCTCCTGTACTTGTCATCTATGGTAAAAACAACCGGCCC
TCAGGGATCCCAGACCGATTCTCTGGCTCCTCCTCAGGCAACACAGCTTCCTTGACCAT
CACTGGGGCTCAGGCGGAAGATGAGGCTGAATATTACTGTAGCTCCAGCACTCGTAATC
ATGTGTTCTTCGGCAGAGGGACCAAGGTCACCGTCCTCGGTGCGGCCGCAACTACCAC
CCCTGCCCCTCGGCCGCCGACTCCGGCCCCAACCATCGCAAGCCAACCCCTCTCCTTG
CGCCCCGAAGCTTGCCGCCCGGCCGCGGGTGGAGCCGTGCATACCCGGGGGCTGGAC
TTTGCCTGCGATATCTACATTTGGGCCCCGCTGGCCGGCACTTGCGGCGTGCTCCTGCT
GTCGCTGGTCATCACCCTTTACTGCAAGAGGGGCCGGAAGAAGCTGCTTTACATCTTCA
AGCAGCCGTTCATGCGGCCCGTGCAGACGACTCAGGAAGAGGACGGATGCTCGTGCAG
ATTCCCTGAGGAGGAAGAGGGGGGATGCGAACTGCGCGTCAAGTTCTCACGGTCCGCC
GACGCCCCCGCATATCAACAGGGCCAGAATCAGCTCTACAACGAGCTGAACCTGGGAA
GGAGAGAGGAGTACGACGTGCTGGACAAGCGACGCGGACGCGACCCGGAGATGGGGG
GGAAACCACGGCGGAAAAACCCTCAGGAAGGACTGTACAACGAACTCCAGAAAGACAA
GATGGCGGAAGCCTACTCAGAAATCGGGATGAAGGGAGAGCGGAGGAGGGGAAAGGG
TCACGACGGGCTGTACCAGGGACTGAGCACCGCCACTAAGGATACCTACGATGCCTTG
CATATGCAAGCACTCCCACCCCGG (SEQ ID NO: 11)

pLTG1901 EF1a MH1P--CD8TM-4-1BB-CD3 zeta amino acid sequence

MLLLVTSLLLCELPHPAFLLIPQVQLQQSGPGLVKPSRTLSLTCAISGDSVSSNSAAWNW
IRQSPSRGLEWLGRTYYRSKWYNDYAVSVKSRITINPDTSKNQFSLQLNSVTPEDTAVYY
CARGKGGKKGGAFDIWGQGTMVTVSSGGGGSGGGGSGGGGSSSELTQDPAVSVALGQT
VRITCQGDSLRSYYASWYQQKPGQAPVLVIYGKNNRPSGIPDRFSGSSSGNTASLTITGAQA
EDEAEYYCSSSTRNHVFFGRGTKVTVLGAAATTTPAPRPPTPAPTIASQPLSLRPEACRP
AAGGAVHTRGLDFACDIYIWAPLAGTCGVLLLSLVITLYCKRGRKKLLYIFKQPFMRPVQ
TTQEEDGCSCRFPEEEEGGCELRVKFSRSADAPAYQQGQNQLYNELNLGRREEYDVLDKR
RGRDPEMGGKPRRKNPQEGLYNELQKDKMAEAYSEIGMKGERRRGKGHDGLYQGLSTAT
KDTYDALHMQALPPR (SEQ ID NO: 12)

FIGURE 2A pLTG1902 Ef1a MH2P CD8TM-4-1BB-CD3 zeta nucleic acid sequence
ATGCTGCTGCTGGTGACCAGCCTGCTGCTGTGCGAACTGCCGCATCCGGCGTTTCTGCT
GATTCCGGAGGTGCAGCTGGTGCAGTCTGGGGGAGGCTTGGTACAGCCTGGCAGGTCC
CAGAGACTCTCCTGTGCAGCCTCTGGATTCACCTTTGATGATTATGCCATGCACTGGGTC
CGGCAAGCTCCAGGGAAGGGCCTGGAGTGGGTCTCAGGTATTAGTTGGAATAGTGGTA
GCATAGGCTATGCGGACTCTGTGAAGGGCCGATTCACCATCTCCAGAGACAACGCCAAG
AACTCCCTGTATCTGCAAATGAACAGTCTGAGAGCTGAGGACACGGCCTTGTATTACTGT
GCAAAAGATATTTCGTCGTCAGCTGGTAACGCTTTTGATATCTGGGGCCAAGGGACAAT
GGTCACCGTCTCTTCAGGAGGTGGCGGGTCTGGTGGAGGCGGTAGCGGCGGTGGCGG
ATCCTCTTCTGAGCTGACTCAGGACCCTGCTGTGTCTGTGGCCTTGGGACAGACAGTCA
GGATCACATGCCAAGGAGACAGACTCAGAAGCTATTATGCAAGCTGGTACCAGCAGAAG
CCAGGACAGGCCCCTGTACTTGTCATCTATGGTAAAAACAACCGGCCCTCAGGGATCCC
AGACCGCTTCTCTGGCTCCGACTCAGGAGACACAGCTTCCTTGACCATCACTGGGGCTC
AGGCGGAAGATGAGGCTGACTATTACTGTCACTCCCGTGACAGTGGTGGTAACCATGTG
GTATTCGGCGGAGGCACCCAGCTGACCGTCCTCGGTGCGGCCGCAACTACCACCCCTG
CCCCTCGGCCGCCGACTCCGGCCCCAACCATCGCAAGCCAACCCCTCTCCTTGCGCCC
CGAAGCTTGCCGCCCGGCCGCGGGTGGAGCCGTGCATACCCGGGGGCTGGACTTTGC
CTGCGATATCTACATTTGGGCCCCGCTGGCCGGCACTTGCGGCGTGCTCCTGCTGTCG
CTGGTCATCACCCTTTACTGCAAGAGGGGCCGGAAGAAGCTGCTTTACATCTTCAAGCA
GCCGTTCATGCGGCCCGTGCAGACGACTCAGGAAGAGGACGGATGCTCGTGCAGATTC
CCTGAGGAGGAAGAGGGGGGATGCGAACTGCGCGTCAAGTTCTCACGGTCCGCCGAC
GCCCCCGCATATCAACAGGGCCAGAATCAGCTCTACAACGAGCTGAACCTGGGAAGGA
GAGAGGAGTACGACGTGCTGGACAAGCGACGCGGACGCGACCCGGAGATGGGGGGGA
AACCACGGCGGAAAAACCCTCAGGAAGGACTGTACAACGAACTCCAGAAAGACAAGATG
GCGGAAGCCTACTCAGAAATCGGGATGAAGGGAGAGCGGAGGAGGGGAAAGGGTCAC
GACGGGCTGTACCAGGGACTGAGCACCGCCACTAAGGATACCTACGATGCCTTGCATAT
GCAAGCACTCCCACCCCGG (SEQ ID NO: 13)

pLTG1902 Ef1a MH2P CD8TM-4-1BB-CD3 zeta amino acid sequence
MLLLVTSLLLCELPHPAFLLIPEVQLVQSGGGLVQPGRSQRLSCAASGFTFDDYAMHWVR
QAPGKGLEWVSGISWNSGSIGYADSVKGRFTISRDNAKNSLYLQMNSLRAEDTALYYCAK
DISSSAGNAFDIWGQGTMVTVSSGGGGSGGGGSGGGGSSSELTQDPAVSVALGQTVRITC
QGDRLRSYYASWYQQKPGQAPVLVIYGKNNRPSGIPDRFSGSDSGDTASLTITGAQAEDE
ADYYCHSRDSGGNHVVFGGGTQLTVLGAAATTTPAPRPPTPAPTIASQPLSLRPEACRPA
AGGAVHTRGLDFACDIYIWAPLAGTCGVLLLSLVITLYCKRGRKKLLYIFKQPFMRPVQT
TQEEDGCSCRFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGLYQGLSTATK
DTYDALHMQALPPR (SEQ ID NO: 14)

FIGURE 2B pLTG1903 Ef1a MH6P CD8TM-4-1BB-CD3 zeta nucleic acid sequence

ATGCTGCTGCTGGTGACCAGCCTGCTGCTGTGCGAACTGCCGCATCCGGCGTTTCTGCT
GATTCCGCAGGTCCAGCTGGTGCAGTCTGGGGCTGAGGTGAAGAAGCCTGGGGCCTCA
GTGAAGGTCTCCTGCAAGGCTTCTGGATACACCTTCACCGGCTACTATATGCACTGGGT
GCGACAGGCCCCTGGACAAGGGCTTGAGTGGATGGGACGGATCAACCCTAACAGTGGT
GGCACAAACTATGCACAGAAGTTTCAGGGCAGGGTCACCATGACCAGGAACACGTCCAT
CAGCACAGCCTACATGGAGCTGAGCAGGCTGAGATCTGACGACACGGCCGTGTATTACT
GTGCGAGATCCGGCTACTACTACGGTTTGGACGTCTGGGGCCAAGGGACCACGGTCAC
CGTCTCCTCAGGAGGTGGCGGGTCTGGTGGAGGCGGTAGCGGCGGTGGCGGATCCCA
GTCTGTGTTGACGCAGCCGCCCTCAGCGTCTGGGACCCCCGGGCAGCGGGTCACCATC
TCTTGTTCTGGAAGTCGCTCCAACATCGGAAGAAACACTGTCAACTGGTATCAACAACTC
CCAGGACTGGCCCCCAAACTCATCATCCAGAGGAGTGATCAGCGGCCCTCAGGGGTCC
CTGACCGATTCTCTGGCTCCAAGTCTGTCACCTCAGCCTCCCTGGCCATCAGTGGGCTC
CGGTCCGAGGATGAGGCTGATTATTACTGCGGAACATGGGATAACAGCCTGAGTGCTTA
TGTCTTCGGAACTGGGACCAAGCTGACCGTCCTCGGTGCGGCCGCAACTACCACCCCT
GCCCCTCGGCCGCCGACTCCGGCCCCAACCATCGCAAGCCAACCCCTCTCCTTGCGCC
CCGAAGCTTGCCGCCCGGCCGCGGGTGGAGCCGTGCATACCCGGGGGCTGGACTTTG
CCTGCGATATCTACATTTGGGCCCCGCTGGCCGGCACTTGCGGCGTGCTCCTGCTGTC
GCTGGTCATCACCCTTTACTGCAAGAGGGGCCGGAAGAAGCTGCTTTACATCTTCAAGC
AGCCGTTCATGCGGCCCGTGCAGACGACTCAGGAAGAGGACGGATGCTCGTGCAGATT
CCCTGAGGAGGAAGAGGGGGGATGCGAACTGCGCGTCAAGTTCTCACGGTCCGCCGA
CGCCCCCGCATATCAACAGGGCCAGAATCAGCTCTACAACGAGCTGAACCTGGGAAGG
AGAGAGGAGTACGACGTGCTGGACAAGCGACGCGGACGCGACCCGGAGATGGGGGG
AAACCACGGCGGAAAAACCCTCAGGAAGGACTGTACAACGAACTCCAGAAAGACAAGAT
GGCGGAAGCCTACTCAGAAATCGGGATGAAGGGAGAGCGGAGGAGGGGAAAGGGTCA
CGACGGGCTGTACCAGGGACTGAGCACCGCCACTAAGGATACCTACGATGCCTTGCAT
ATGCAAGCACTCCCACCCCGG (SEQ ID NO: 15)

pLTG1903 Ef1a MH6P CD8TM-4-1BB-CD3 zeta amino acid sequence

MLLLVTSLLLCELPHPAFLLIPQVQLVQSGAEVKKPGASVKVSCKASGYTFTGYYMHWVR
QAPGQGLEWMGRINPNSGGTNYAQKFQGRVTMTRNTSISTAYMELSRLRSDDTAVYYCAR
SGYYYGLDVWGQGTTVTVSSGGGGSGGGGSGGGGSQSVLTQPPSASGTPGQRVTISCSG
SRSNIGRNTVNWYQQLPGLAPKLIIQRSDQRPSGVPDRFSGSKSVTSASLAISGLRSEDEA
DYYCGTWDNSLSAYVFGTGTKLTVLGAAATTTPAPRPPTPAPTIASQPLSLRPEACRPAA
GGAVHTRGLDFACDIYIWAPLAGTCGVLLLSLVITLYCKRGRKKLLYIFKQPFMRPVQTT
QEEDGCSCRFPEEEEGGCELRVKFSRSADAPAYQQGQNQLYNELNLGRREEYDVLDKRRG
RDPEMGGKPRRKNPQEGLYNELQKDKMAEAYSEIGMKGERRRGKGHDGLYQGLSTATKD
TYDALHMQALPPR (SEQ ID NO: 16)

FIGURE 2C pLTG1904 Ef1a M1-4S CD8TM-4-1BB-CD3 zeta nucleic acid sequence

ATGCTGCTGCTGGTGACCAGCCTGCTGCTGTGCGAACTGCCGCATCCGGCGTTTCTGCT
GATTCCGGAGGTCCAGCTGGTACAGTCTGGGGGAGGCTTGGTACAGCCTGGGGGGTCC
CTGAGACTCTCCTGTGCAGCCTCTGGATTCACCTTTGATGATTATGCCATGCACTGGGTC
CGGCAAGCTCCAGGGAAGGGCCTGGAGTGGGTCTCAGGTATTAGTTGGAATAGTGGTA
GCATAGGCTATGCGGACTCTGTGAAGGGCCGATTCACCATCTCCAGAGACAACGCCAAG
AACTCCCTGTATCTGCAAATGAACAGTCTGAGAGCTGAGGACACGGCCTTGTATTACTGT
GCAAAAGATTTATCGTCAGTGGCTGGACCCTTTAACTACTGGGGCCAGGGCACCCTGGT
CACCGTCTCCTCAGGAGGTGGCGGGTCTGGTGGAGGCGGTAGCGGCGGTGGCGGATC
CTCTTCTGAGCTGACTCAGGACCCTGCTGTGTCTGTGGCCTTGGGACAGACAGTCAGGA
TCACATGCCAAGGAGACAGCCTCAGAAGCTATTATGCAAGCTGGTACCAGCAGAAGCCA
GGACAGGCCCCTGTACTTGTCATCTATGGTAAAAACAACCGGCCCTCAGGGATCCCAGA
CCGATTCTCTGGCTCCAGCTCAGGAAACACAGCTTCCTTGACCATCACTGGGGCTCAGG
CGGAGGATGAGGCTGACTATTACTGTAACTCCCGGGACAGCAGTGGTAACCATCTGGTA
TTCGGCGGAGGCACCCAGCTGACCGTCCTCGGTGCGGCCGCAACTACCACCCCTGCCC
CTCGGCCGCCGACTCCGGCCCCAACCATCGCAAGCCAACCCCTCTCCTTGCGCCCCGA
AGCTTGCCGCCCGGCCGCGGGTGGAGCCGTGCATACCCGGGGGCTGGACTTTGCCTG
CGATATCTACATTTGGGCCCCGCTGGCCGGCACTTGCGGCGTGCTCCTGCTGTCGCTG
GTCATCACCCTTTACTGCAAGAGGGGCCGGAAGAAGCTGCTTTACATCTTCAAGCAGCC
GTTCATGCGGCCCGTGCAGACGACTCAGGAAGAGGACGGATGCTCGTGCAGATTCCCT
GAGGAGGAAGAGGGGGGATGCGAACTGCGCGTCAAGTTCTCACGGTCCGCCGACGCC
CCCGCATATCAACAGGGCCAGAATCAGCTCTACAACGAGCTGAACCTGGGAAGGAGAG
AGGAGTACGACGTGCTGGACAAGCGACGCGGACGCGACCCGGAGATGGGGGGGAAAC
CACGGCGGAAAAACCCTCAGGAAGGACTGTACAACGAACTCCAGAAAGACAAGATGGC
GGAAGCCTACTCAGAAATCGGGATGAAGGGAGAGCGGAGGAGGGGAAAGGGTCACGA
CGGGCTGTACCAGGGACTGAGCACCGCCACTAAGGATACCTACGATGCCTTGCATATGC
AAGCACTCCCACCCCGG (SEQ ID NO: 17)

pLTG1904 Ef1a M1-4S CD8TM-4-1BB-CD3 zeta amino acid sequence
MLLLVTSLLLCELPHPAFLLIPEVQLVQSGGGLVQPGGSLRLSCAASGFTFDDYAMHWVR
QAPGKGLEWVSGISWNSGSIGYADSVKGRFTISRDNAKNSLYLQMNSLRAEDTALYYCAK
DLSSVAGPFNYWGQGTLVTVSSGGGGSGGGGSGGGGSSSELTQDPAVSVALGQTVRITC
QGDSLRSYYASWYQQKPGQAPVLVIYGKNNRPSGIPDRFSGSSSGNTASLTITGAQAEDEA
DYYCNSRDSSGNHLVFGGGTQLTVLGAAATTTPAPRPPTPAPTIASQPLSLRPEACRPAA
GGAVHTRGLDFACDIYIWAPLAGTCGVLLLSLVITLYCKRGRKKLLYIFKQPFMRPVQTT
QEEDGCSCRFPEEEEGGCELRVKFSRSADAPAYQQGQNQLYNELNLGRREEYDVLDKRRG
RDPEMGGKPRRKNPQEGLYNELQKDKMAEAYSEIGMKGERRRGKGHDGLYQGLSTATKD
TYDALHMQALPPR (SEQ ID NO: 18)

FIGURE 2D

COMPOSITIONS AND METHODS FOR TREATING CANCER WITH ANTI-MESOTHELIN IMMUNOTHERAPY

CROSS-REFERENCE TO RELATED APPLICATIONS

This application is a continuation of U.S. patent application Ser. No. 16/252,158, filed Jan. 18, 2019, now issued U.S. Pat. No. 10,550,179, which is a continuation of U.S. patent application Ser. No. 15/866,222, filed Jan. 9, 2018, now issued U.S. Pat. No. 10,183,993, and claims the benefit of priority under 35 U.S.C. Section 119(e) to U.S. Provisional Patent Application No. 62/444,201, filed on Jan. 9, 2017, the entire contents of which are incorporated herein by reference.

STATEMENT REGARDING FEDERALLY SPONSORED RESEARCH OR DEVELOPMENT

This invention was created in the performance of a Cooperative Research and Development Agreement with the National Institutes of Health, an Agency of the Department of Health and Human Services. The Government of the United States has certain rights in this invention.

SEQUENCE LISTING

This application contains a Sequence Listing that has been submitted electronically as an ASCII text file named "42449-0012003 SL_ST25.txt." The ASCII text file, created on Jan. 22, 2023, is 48,461 bytes in size. The material in the ASCII text file is hereby incorporated by reference in its entirety.

FIELD OF THE DISCLOSURE

This application relates to the field of cancer, particularly to mesothelin antigen binding domains and chimeric antigen receptors (CARs) containing such mesothelin antigen binding domains and methods of use thereof.

BACKGROUND

Cancer is one of the most deadly threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult.

Mesothelin is a 40 kDa glycosylphosphatidyl inositol-linked membrane glycoprotein whose expression in normal individuals is restricted to the mesothelial cells lining pleura, peritoneum and pericardium. By contrast, mesothelin is overexpressed by a number of solid tumors, including malignant mesothelioma, ovarian, stomach, lung, and pancreatic adenocarcinoma, as well as bile duct carcinoma and triple negative breast cancer (Ordonez N G, Am J Surg Pathol 1993; 27:1418-28, Hassan R, Laszik Z G, Lerner M, Raffeld M, Postier R, Brackett D. *Am J Clin Pathol* 2005; 124:838-45; Chou J, et al. *Breast Cancer Res Treat* 2012; 133:799-804). The biological function of mesothelin is still unclear; however mesothelin binds to CA125, a plasma glycoprotein on tumor cells, suggesting that mesothelin may contribute to peritoneal and pleural metastasis (Kaneko, et al., 2009, J Biol Chem 284: 3739-3749; Rump, et al., 2004, J Biol Chem 279: 9190-9198). Mesothelin expression is associated with chemoresistance, shorter disease-free survival and worse overall survival of patients with epithelial ovarian cancer (EOC) (Cheng, et al., 2009, Br J Cancer 100: 1144-1153). Accordingly, mesothelin represents an attractive target for immune-based therapies. Based on frequency of tumor expression, primary targets of anti-mesothelin therapy are mesotheliomas and pancreatic adenocarcinomas (close to 100% tumors express antigen), followed by ovarian cancers (67-100% tumors express antigen) and lung adenocarcinomas (41-53% are mesothelin positive), reviewed in Raffit Hassan, Mitchell Ho. Eur J Cancer. 2008 January; 44(1): 46-53. First cancer therapeutic antibody targeting mesothelin, K1, was derived from a mouse hybridoma [Chang K, Pastan I, Willingham M C. *Int J Cancer* 1992; 50:373-81.]. Subsequently, a greater affinity anti-mesothelin antibody termed SS1 was developed by phage display and hot spot mutagenesis [Chowdhury P S, Viner J L, Beers R, Pastan I. *Proc Natl Acad Sci USA* 1998; 95:669-74; Chowdhury P S, Pastan I, *Nat Biotech* 1999; 17:568-72].

Chimeric Antigen Receptors (CARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4): e23621). The antigen-binding motif of a CAR is commonly fashioned after an single chain Fragment variable (scFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered. Alternate cell targets for CAR expression (such as NK or gamma-delta T cells) are also under development (Brown C E et al Clin Cancer Res. 2012; 18(8):2199-209; Lehner M et al. PLoS One. 2012; 7 (2): e31210). There remains significant work with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the scFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-ζ chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al J Immunol. 2009; 183 (9): 5563-74). With the advent of new technology, the activation of T cells with beads linked to anti-CD3 and anti-CD28 antibody, and the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B cell precursor acute lymphoblastic leukemia, Blood. 2013; 121 (7):1165-74; Kochenderfer J N et al. Blood. 2012; 119 (12):2709-20). This is borne out by the clinical success of CD19-specific CARS that are in a second generation CD28/CD3-ζ (Lee D W et al. American Society of Hematology Annual Meeting. New Orleans, LA; Dec. 7-10, 2013) and a CD137/CD3-ζ signaling format (Porter D L et al. N Engl J Med. 2011; 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15(18):5852-60). Equally important are the culture conditions under which the CAR T-cell populations were cultured.

Current challenges in the more widespread and effective adaptation of CAR therapy for cancer relate to a paucity of compelling targets. Creating binders to cell surface antigens is now readily achievable, but discovering a cell surface antigen that is specific for tumor while sparing normal tissues remains a formidable challenge. One potential way to imbue greater target cell specificity to CAR-expressing T cells is to use combinatorial CAR approaches. In one system, the CD3-ζ and CD28 signal units are split between two different CAR constructs expressed in the same cell; in another, two CARs are expressed in the same T cell, but one has a lower affinity and thus requires the alternate CAR to be engaged first for full activity of the second (Lanitis E et al. Cancer Immunol Res. 2013; 1(1):43-53; Kloss C C et al. Nat Biotechnol. 2013; 31(1):71-5). A second challenge for the generation of a single scFv-based CAR as an immunotherapeutic agent is tumor cell heterogeneity. At least one group has developed a CAR strategy for glioblastoma whereby the effector cell population targets multiple antigens (HER2, IL-13Ra, EphA2) at the same time in the hope of avoiding the outgrowth of target antigen-negative populations. (Hegde M et al. Mol Ther. 2013; 21(11):2087-101).

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with AP1903 demonstrates one way in which a powerful switch that can control T-cell populations can be initiated pharmacologically (Di Stasi A et al. N Engl J Med. 2011; 365(18):1673-83). The creation of effector T-cell populations that are immune to the negative regulatory effects of transforming growth factor-β by the expression of a decoy receptor further demonstrates that degree to which effector T cells can be engineered for optimal antitumor activity (Foster A E et al. J Immunother. 2008; 31(5):500-5).

Thus, while it appears that CARs can trigger T-cell activation in a manner similar to an endogenous T-cell receptor, a major impediment to the clinical application of this technology to date has been limited in vivo expansion of CAR+ T cells, rapid disappearance of the cells after infusion, and disappointing clinical activity. Although several attempts to target mesothelin-positive tumors have been made by other groups, including recent work that has shown that human T cells bearing an anti-human mesothelin CAR of mouse origin (referred to as SS1) exhibit MHC-independent effector functions in vitro and induce the regression of human mesothelioma xenografts in vivo in immunodeficient mice (Carpenito, et al., 2009, Proc Natl Acad Sci USA 106: 3360-3365), a number of challenges to this approach became apparent, including toxicity to by-stander cells, lack of efficacy, or the need for localized tumor delivery. Accordingly, there is an urgent and long felt need in the art for discovering compositions and methods for treatment of cancer using CARs that can exhibit intended therapeutic attributes without the aforementioned short comings.

The present invention addresses these needs by providing CAR compositions and therapeutic methods that can be used to treat cancers and other diseases and/or conditions. In particular, the present invention as disclosed and described herein provides CARs that may be used the treatment of diseases, disorders or conditions associated with dysregulated expression of mesothelin and which CARS contain mesothelin antigen binding domains that exhibit a high surface expression on transduced T cells, exhibit a high degree of cytolysis and transduced T cell in vivo expansion and persistence.

SUMMARY

Novel anti-mesothelin antibodies or antigen binding domains thereof and chimeric antigen receptors (CARs) that contain such mesothelin antigen binding domains are provided herein, as well as host cells (e.g., T cells) expressing the receptors, and nucleic acid molecules encoding the receptors. The CARs exhibit a high surface expression on transduced T cells, with a high degree of cytolysis and transduced T cell expansion and persistence in vivo. Methods of using the disclosed CARs, host cells, and nucleic acid molecules are also provided, for example, to treat a cancer in a subject.

Thus, in one aspect, an isolated polynucleotide encoding a human anti-mesothelin antibody or a fragment thereof is provided comprising a nucleic acid sequence selected from the group consisting of SEQ ID NOs: 1, 3, 5 and 7.

In one embodiment, an isolated polynucleotide encoding a fully human anti-mesothelin antibody or a fragment thereof is provided, wherein the antibody or a fragment thereof comprises a fragment selected from the group consisting of an Fab fragment, an $F(ab')_2$ fragment, an Fv fragment, and a single chain Fv (scFv).

In one embodiment, an isolated polynucleotide encoding a fully human anti-mesothelin antibody or a fragment thereof is provided, wherein the antibody or a fragment thereof comprises an amino acid sequence selected from the group consisting of SEQ ID NOs: 2, 4, 6, and 8.

In one aspect, an isolated nucleic acid molecule encoding a chimeric antigen receptor (CAR) is provided comprising, from N-terminus to C-terminus, at least one mesothelin antigen binding domain encoded by a nucleotide sequence comprising a nucleic acid sequence selected from the group consisting of SEQ ID NOs: 1, 3, 5 and 7, at least one transmembrane domain, and at least one intracellular signaling domain.

In one embodiment, an isolated nucleic acid molecule encoding the CAR is provided wherein the encoded extracellular mesothelin antigen binding domain comprises at least one single chain variable fragment of an antibody that binds to mesothelin.

In another embodiment, an isolated nucleic acid molecule encoding the CAR is provided wherein the encoded extracellular mesothelin antigen binding domain comprises at least one heavy chain variable region of an antibody that binds to mesothelin.

In yet another embodiment, an isolated nucleic acid molecule encoding the CAR is provided wherein the encoded CAR extracellular mesothelin antigen binding domain further comprises at least one lipocalin-based antigen binding antigen (anticalins) that binds to mesothelin.

In one embodiment, an isolated nucleic acid molecule is provided wherein the encoded extracellular mesothelin antigen binding domain is connected to the transmembrane domain by a linker domain.

In another embodiment, an isolated nucleic acid molecule encoding the CAR is provided wherein the encoded mesothelin extracellular antigen binding domain is preceded by a sequence encoding a leader or signal peptide.

In yet another embodiment, an isolated nucleic acid molecule encoding the CAR is provided comprising at least one mesothelin antigen binding domain encoded by a nucleotide sequence comprising a nucleic acid sequence selected from the group consisting of SEQ ID NOs: 1, 3, 5 and 7, and wherein the CAR additionally encodes an extracellular antigen binding domain targets an antigen that includes, but is not limited to, CD19, CD20, CD22, ROR1, mesothelin, CD33, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, or any combination thereof.

In certain embodiments, an isolated nucleic acid molecule encoding the CAR is provided wherein the additionally encoded extracellular antigen binding domain comprises an anti-CD19 scFV antigen binding domain, an anti-CD20 scFV antigen binding domain, an anti-CD22 scFV antigen binding domain, an anti-ROR1 scFV antigen binding domain, an anti-mesothelin scFV antigen binding domain, an anti-CD33 scFV antigen binding domain, an anti-CD38 scFV antigen binding domain, an anti-CD123 (IL3RA) scFV antigen binding domain, an anti-CD138 scFV antigen binding domain, an anti-BCMA (CD269) scFV antigen binding domain, an anti-GPC2 scFV antigen binding domain, an anti-GPC3 scFV antigen binding domain, an anti-FGFR4 scFV antigen binding domain, an anti-c-Met scFV antigen binding domain, an anti-PMSA scFV antigen binding domain, an anti-glycolipid F77 scFV antigen binding domain, an anti-EGFRvIII scFV antigen binding domain, an anti-GD-2 scFV antigen binding domain, an anti-NY-ESo-1 TCR scFV antigen binding domain, an anti-MAGE A3 TCR scFV antigen binding domain, or an amino acid sequence with 85%, 90%, 95%, 96%, 97%, 98% or 99% identity thereof, or any combination thereof.

In one aspect, the CARs provided herein further comprise a linker or spacer domain.

In one embodiment, an isolated nucleic acid molecule encoding the CAR is provided wherein the extracellular mesothelin antigen binding domain, the intracellular signaling domain, or both are connected to the transmembrane domain by a linker or spacer domain.

In one embodiment, an isolated nucleic acid molecule encoding the CAR is provided wherein the encoded linker domain is derived from the extracellular domain of CD8 or CD28, and is linked to a transmembrane domain.

In another embodiment, an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In yet another embodiment, an isolated nucleic acid molecule encoding the CAR is provided wherein the encoded intracellular signaling domain further comprises a CD3 zeta intracellular domain.

In one embodiment, an isolated nucleic acid molecule encoding the CAR is provided wherein the encoded intracellular signaling domain is arranged on a C-terminal side relative to the CD3 zeta intracellular domain.

In another embodiment, an isolated nucleic acid molecule encoding the CAR is provided wherein the encoded at least one intracellular signaling domain comprises a costimulatory domain, a primary signaling domain, or a combination thereof.

In further embodiments, an isolated nucleic acid molecule encoding the CAR is provided wherein the encoded at least one costimulatory domain comprises a functional signaling domain of OX40, CD70, CD27, CD28, CDS, ICAM-1, LFA-1 (CD11a/CD18), ICOS (CD278), DAP10, DAP12, and 4-1BB (CD137), or a combination thereof.

In one embodiment, an isolated nucleic acid molecule encoding the CAR is provided that further contains a leader sequence or signal peptide wherein the leader or signal peptide nucleotide sequence comprises the nucleotide sequence of SEQ ID NO: 9.

In yet another embodiment, an isolated nucleic acid molecule encoding the CAR is provided wherein the encoded leader sequence comprises the amino acid sequence of SEQ ID NO: 10.

In one aspect, a chimeric antigen receptor (CAR) is provided herein comprising, from N-terminus to C-terminus, at least one mesothelin antigen binding domain, at least one transmembrane domain, and at least one intracellular signaling domain.

In one embodiment, a CAR is provided wherein the extracellular mesothelin antigen binding domain comprises at least one single chain variable fragment of an antibody that binds to the antigen, or at least one heavy chain variable region of an antibody that binds to the antigen, or a combination thereof.

In another embodiment, a CAR is provided wherein the at least one transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In some embodiments, the CAR is provided wherein CAR additionally encodes an extracellular antigen binding domain comprising CD19, CD20, CD22, ROR1, mesothelin, CD33, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, or an amino acid sequence with 85%, 90%, 95%, 96%, 97%, 98% or 99% identity thereof, or any combination thereof.

In one embodiment, the CAR is provided wherein the extracellular antigen binding domain comprises an anti-CD19 scFV antigen binding domain, an anti-CD20 scFV antigen binding domain, an anti-CD22 scFV antigen binding domain, an anti-ROR1 scFV antigen binding domain, an anti-mesothelin scFV antigen binding domain, an anti-CD33 scFV antigen binding domain, an anti-CD38 scFV antigen binding domain, an anti-CD123 (IL3RA) scFV antigen binding domain, an anti-CD138 scFV antigen binding domain, an anti-BCMA (CD269) scFV antigen binding domain, an anti-GPC2 scFV antigen binding domain, an anti-GPC3 scFV antigen binding domain, an anti-FGFR4 scFV antigen binding domain, an anti-c-Met scFV antigen binding domain, an anti-PMSA scFV antigen binding domain, an anti-glycolipid F77 scFV antigen binding domain, an anti-EGFRvIII scFV antigen binding domain, an anti-GD-2 scFV antigen binding domain, an anti-NY-ESo-1 TCR scFV antigen binding domain, an anti-MAGE A3 TCR scFV antigen binding domain, or an amino acid sequence with 85%, 90%, 95%, 96%, 97%, 98% or 99% identity thereof, or any combination thereof.

In another embodiment, a CAR is provided wherein the at least one intracellular signaling domain comprises a costimulatory domain and a primary signaling domain.

In yet another embodiment, a CAR is provided wherein the at least one intracellular signaling domain comprises a costimulatory domain comprising a functional signaling domain of a protein selected from the group consisting of OX40, CD70, CD27, CD28, CDS, ICAM-1, LFA-1 (CD11a/CD18), ICOS (CD278), DAP10, DAP12, and 4-1BB (CD137), or a combination thereof.

In one embodiment, the nucleic acid sequence encoding a CAR comprises the nucleic acid sequence of SEQ ID NO: 11 (pLTG1901 EF1a MH1P-CD8TM-4-1BB-CD3 zeta nucleic acid sequence (FIG. 2A)). In one embodiment, the nucleic acid sequence encodes a CAR comprising the amino acid sequence of SEQ ID NO: 12 (pLTG1901 EF1a MH1P-CD8TM-4-1BB-CD3 zeta amino acid sequence) (FIG. 2A)).

In another embodiment, the nucleic acid sequence encoding a CAR comprises the nucleic acid sequence of SEQ ID NO: 13. (pLTG1902 Ef1a MH2P CD8TM-4-1BB-CD3 zeta nucleic acid sequence (FIG. 2B)). In one embodiment, the nucleic acid sequence encodes a CAR comprising the amino acid sequence of SEQ ID NO: 14. (pLTG1902 Ef1a MH2P CD8TM-4-1BB-CD3 zeta amino acid sequence (FIG. 2B)).

In another embodiment, the nucleic acid sequence encoding a CAR comprises the nucleic acid sequence of SEQ ID NO: 15 (pLTG1903 Ef1a MH6P CD8TM-4-1BB-CD3 zeta nucleic acid sequence (FIG. 2C)). In one embodiment, the nucleic acid sequence encodes a CAR comprising the amino acid sequence of SEQ ID NO: 16 (pLTG1903 Ef1a MH6P CD8TM-4-1BB-CD3 zeta amino acid sequence (FIG. 2C)).

In another embodiment, the nucleic acid sequence encoding a CAR comprises the nucleic acid sequence of SEQ ID NO: 17 (pLTG1904 Ef1a M1-45 CD8TM-4-1BB-CD3 zeta nucleic acid sequence (FIG. 2D)). In one embodiment, the nucleic acid sequence encodes a CAR comprising the amino acid sequence of SEQ ID NO: 18 (pLTG1904 Ef1a M1-45 CD8TM-4-1BB-CD3 zeta amino acid sequence (FIG. 2D)).

In one aspect, the CARs disclosed herein are modified to express or contain a detectable marker for use in diagnosis, monitoring, and/or predicting the treatment outcome such as progression free survival of cancer patients or for monitoring the progress of such treatment.

In one embodiment, the nucleic acid molecule encoding the disclosed CARS can be contained in a vector, such as a viral vector. The vector is a DNA vector, an RNA vector, a plasmid vector, a cosmid vector, a herpes virus vector, a measles virus vector, a lentivirus vector, adenoviral vector, or a retrovirus vector, or a combination thereof.

In certain embodiments, the vector further comprises a promoter wherein the promoter is an inducible promoter, a tissue specific promoter, a constitutive promoter, a suicide promoter or any combination thereof.

In yet another embodiment, the vector expressing the CAR can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD).

In another aspect, host cells including the nucleic acid molecule encoding the CAR are also provided. In some embodiments, the host cell is a T cell, such as a primary T cell obtained from a subject. In one embodiment, the host cell is a CD8+ T cell.

In yet another aspect, a pharmaceutical composition is provided comprising an anti-tumor effective amount of a population of human T cells, wherein the T cells comprise a nucleic acid sequence that encodes a chimeric antigen receptor (CAR), wherein the CAR comprises at least one extracellular antigen binding domain comprising a mesothelin antigen binding domain comprising the amino acid sequence of SEQ ID NO. 2, 4, 6, and 8, at least one linker domain, at least one transmembrane domain, and at least one intracellular signaling domain, wherein the T cells are T cells of a human having a cancer. The cancer includes, inter alia, a hematological cancer such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma) or multiple myeloma, or a combination thereof.

In one embodiment, a pharmaceutical composition is provided wherein the at least one transmembrane domain of the CAR contains a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In another embodiment, a pharmaceutical composition is provided wherein the human cancer includes an adult carcinoma comprising oral and pharynx cancer (tongue, mouth, pharynx, head and neck), digestive system cancers (esophagus, stomach, small intestine, colon, rectum, anus, liver, interhepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In yet another embodiment, a pharmaceutical composition is provided comprising an anti-tumor effective amount of a population of human T cells of a human having a cancer wherein the cancer is a refractory cancer non-responsive to one or more chemotherapeutic agents. The cancer includes hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another aspect, methods of making CAR-containing T cells (hereinafter "CAR-T cells") are provided. The methods include transducing a T cell with a vector or nucleic acid molecule encoding a disclosed CAR that specifically binds mesothelin, thereby making the CAR-T cell.

In yet another aspect, a method of generating a population of RNA-engineered cells is provided that comprises introducing an in vitro transcribed RNA or synthetic RNA of a nucleic acid molecule encoding a disclosed CAR into a cell of a subject, thereby generating a CAR cell.

In yet another aspect, a method for diagnosing a disease, disorder or condition associated with the expression of mesothelin on a cell, is provided comprising a) contacting the cell with a human anti-mesothelin antibody or fragment thereof, wherein the antibody or a fragment thereof comprises an amino acid sequence selected from the group consisting of SEQ ID NOs: 2, 4, 6, and 8; and b) detecting the presence of mesothelin wherein the presence of mesothelin diagnoses for the disease, disorder or condition associated with the expression of mesothelin.

In one embodiment, the disease, disorder or condition associated with the expression of mesothelin is cancer including hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another embodiment, a method of diagnosing, prognosing, or determining risk of a mesothelin-related disease in a mammal, is provided comprising detecting the expression of mesothelin in a sample derived from the mammal comprising: a) contacting the sample with a human anti-mesothelin antibody or fragment thereof, wherein the antibody or a fragment thereof comprises an amino acid sequence selected from the group consisting of SEQ ID NOs: 2, 4, 6, and 8; and b) detecting the presence of mesothelin wherein the presence of mesothelin diagnoses for a mesothelin-related disease in the mammal.

In another embodiment, a method of inhibiting mesothelin-dependent T cell inhibition, is provided comprising contacting a cell with a human anti-mesothelin antibody or fragment thereof, wherein the antibody or a fragment thereof comprises an amino acid sequence selected from the group consisting of SEQ ID NOs: 2, 4, 6, and 8. In one embodiment, the cell is selected from the group consisting of a mesothelin-expressing tumor cell, a tumor-associated macrophage, and any combination thereof.

In another embodiment, a method of blocking T-cell inhibition mediated by a mesothelin-expressing cell and altering the tumor microenvironment to inhibit tumor growth in a mammal, is provided comprising administering to the mammal an effective amount of a composition comprising an isolated anti-mesothelin antibody or fragment thereof, wherein the antibody or a fragment thereof comprises an amino acid sequence selected from the group consisting of SEQ ID NOs: 2, 4, 6, and 8. In one embodiment, the cell is selected from the group consisting of a mesothelin-expressing tumor cell, a tumor-associated macrophage, and any combination thereof.

In another embodiment, a method of inhibiting, suppressing or preventing immunosuppression of an anti-tumor or anti-cancer immune response in a mammal, is provided comprising administering to the mammal an effective amount of a composition comprising an isolated anti-mesothelin antibody or fragment thereof, wherein the antibody or a fragment thereof comprises an amino acid sequence selected from the group consisting of SEQ ID NOs: 2, 4, 6, and 8. In one embodiment, the antibody or fragment thereof inhibits the interaction between a first cell with a T cell, wherein the first cell is selected from the group consisting of a mesothelin-expressing tumor cell, a tumor-associated macrophage, and any combination thereof.

In another aspect, a method is provided for inducing an anti-tumor immunity in a mammal comprising administering to the mammal a therapeutically effective amount of a T cell transduced with vector or nucleic acid molecule encoding a disclosed CAR.

In another embodiment, a method of treating or preventing cancer in a mammal is provided comprising administering to the mammal one or more of the disclosed CARs, in an amount effective to treat or prevent cancer in the mammal. The method includes administering to the subject a therapeutically effective amount of host cells expressing a disclosed CAR that specifically binds mesothelin and/or one or more of the aforementioned antigens, under conditions sufficient to form an immune complex of the antigen binding domain on the CAR and the extracellular domain of mesothelin and/or one or more of the aforementioned antigens in the subject.

In yet another embodiment, a method is provided for treating a mammal having a disease, disorder or condition associated with an elevated expression of a tumor antigen, the method comprising administering to the subject a pharmaceutical composition comprising an anti-tumor effective amount of a population of T cells, wherein the T cells comprise a nucleic acid sequence that encodes a chimeric antigen receptor (CAR), wherein the CAR includes at least one extracellular mesothelin antigen binding domain comprising the amino acid sequence of SEQ ID NO. 2, 4, 6, or 8, or any combination thereof, at least one linker or spacer domain, at least one transmembrane domain, at least one intracellular signaling domain, and wherein the T cells are T cells of the subject having cancer.

In yet another embodiment, a method is provided for treating cancer in a subject in need thereof comprising administering to the subject a pharmaceutical composition comprising an anti-tumor effective amount of a population of T cells, wherein the T cells comprise a nucleic acid sequence that encodes a chimeric antigen receptor (CAR), wherein the CAR comprises at least one mesothelin antigen binding domain comprising the amino acid sequence of SEQ ID NO. 2, 4, 6, or 8, or any combination thereof, at least one linker or spacer domain, at least one transmembrane domain, at least one intracellular signaling domain, wherein the T cells are T cells of the subject having cancer. In some embodiments of the aforementioned methods, the at least one transmembrane domain comprises a transmembrane the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In yet another embodiment, a method is provided for generating a persisting population of genetically engineered T cells in a human diagnosed with cancer. In one embodiment, the method comprises administering to a human a T cell genetically engineered to express a CAR wherein the CAR comprises at least one mesothelin antigen binding domain comprising the amino acid sequence of SEQ ID NO. 2, 4, 6, or 8, or any combination thereof, at least one transmembrane domain, and at least one intracellular signaling domain wherein the persisting population of genetically engineered T cells, or the population of progeny of the T cells, persists in the human for at least one month, two months, three months, four months, five months, six months, seven months, eight months, nine months, ten months, eleven months, twelve months, two years, or three years after administration.

In one embodiment, the progeny T cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using one or more of the CARs disclosed herein, In yet another aspect, a kit is provided for making a chimeric antigen receptor T-cell as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

It will be understood that the CARs, host cells, nucleic acids, and methods are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE FIGURES

FIGS. 2A-D depict several chimeric antigen receptors (CARs) containing novel extracellular mesothelin antigen binding domain sequences. The general scheme for the CARs includes, from the N terminus to the C terminus, a Signal peptide, anti-mesothelin scFv, extracellular linker, transmembrane, 4-1BB, CD3 zeta. FIG. 2A depicts a lentiviral vector expressing the CAR containing pLTG1901 EF1a MH1P mesothelin scFv binder CD8TM-4-1BB-CD3 zeta nucleic acid sequence and the encoded amino acid sequence. FIG. 2B depicts a lentiviral vector expressing the CAR containing pLTG1902 Ef1a MH2P mesothelin scFv binder CD8TM-4-1BB-CD3 zeta nucleic acid sequence and the encoded amino acid sequence. FIG. 2C depicts a lentiviral vector expressing the CAR containing pLTG1903 Ef1a MH6P mesothelin scFv binder CD8TM-4-1BB-CD3 zeta nucleic acid sequence and the encoded amino acid sequence. FIG. 2D depicts a lentiviral vector expressing the CAR containing pLTG1904 Ef1a M1-4S mesothelin scFv binder CD8TM-4-1BB-CD3 zeta nucleic acid sequence and the encoded amino acid sequence.

DETAILED DESCRIPTION

Definitions

Figure 1:
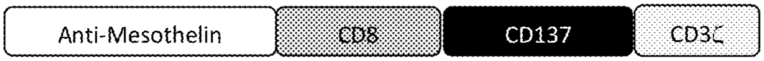
FIG. 1 depicts a schematic of the general domain structure of CARs with novel extracellular mesothelin antigen binding domain sequences A chimeric antigen receptor is composed of an extracellular mesothelin-binding ScFv domain, a CD8 spacer and transmembrane domain, an intracellular signaling CD137 costimulatory domain and CD3 z signaling domain.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

The term "about" when referring to a measurable value such as an amount, a temporal duration, and the like, is meant to encompass variations of .+-.20% or in some instances .+-.10%, or in some instances .+-.5%, or in some instances .+-.1%, or in some instances .+-.0.1% from the specified value, as such variations are appropriate to perform the disclosed methods.

Unless otherwise noted, the technical terms herein are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnol-*

*ogy: a Comprehensive Desk Reference*, published by VCH Publishers, Inc., 1995; and other similar references.

The present disclosure provides for mesothelin antibodies or fragments thereof as well as chimeric antigen receptors (CARs) having such mesothelin antigen binding domains. The enhancement of the functional activity of the CAR directly relates to the enhancement of functional activity of the CAR-expressing T cell. As a result of one or more of these modifications, the CARs exhibit both a high degree of cytokine-induced cytolysis and cell surface expression on transduced T cells, along with an increased level of in vivo T cell expansion and persistence of the transduced CAR-expressing T cell.

The unique ability to combine functional moieties derived from different protein domains has been a key innovative feature of Chimeric Antigen Receptors (CARs). The choice of each of these protein domains is a key design feature, as is the way in which they are specifically combined. Each design domain is an essential component that can be used across different CAR platforms to engineer the function of lymphocytes. For example, the choice of the extracellular binding domain can make an otherwise ineffective CAR be effective.

The invariable framework components of the immunoglobulin-derived protein sequences used to create the extracellular antigen binding domain of a CAR can either be entirely neutral, or they can self-associate and drive the T cell to a state of metabolic exhaustion, thus making the therapeutic T cell expressing that CAR far less effective. This occurs independently of the antigen binding function of this CAR domain. Furthermore, the choice of the intracellular signaling domain(s) also can govern the activity and the durability of the therapeutic lymphocyte population used for immunotherapy. While the ability to bind target antigen and the ability to transmit an activation signal to the T cell through these extracellular and intracellular domains, respectively, are important CAR design aspects, what has also become apparent is that the choice of the source of the extracellular antigen binding fragments can have a significant effect on the efficacy of the CAR and thereby have a defining role for the function and clinical utility of the CAR.

Surprisingly and unexpectedly it has now been discovered that use of an entirely human extracellular mesothelin ScFv antigen binding domain in a CAR, rather than using mouse-derived mesothelin ScFv antigen binding fragments to generate anti-mesothelin CARs which are prone to induce anti-mouse immune response and CAR T elimination in a host (c.f., the UPenn-sponsored clinical trial using mouse derived SS1 ScFv sequence, NCT02159716), also determines the functional activity of a CAR-expressing T cell. The CARs disclosed herein are expressed at a high level in a cell. A cell expressing the CAR has a high in vivo proliferation rate, produces large amounts of cytokines, and has a high cytotoxic activity against a cell having, on its surface, a mesothelin antigen to which a CAR binds. The use of a human extracellular mesothelin antigen binding domain results in generation of a CAR that functions better in vivo, while avoiding the induction of anti-CAR immunity in the host immune response and the killing of the CAR T cell population. The CARs expressing the entirely human extracellular mesothelin ScFv antigen binding domain exhibit superior activities/properties including i) prevention of poor CAR T persistence and function as seen with mouse-derived binding sequences; ii) lack of regional (i.e. intrapleural) delivery of the CAR to be efficacious; and iii) ability to generate CAR T cell designs based both on binders with high and low affinity to mesothelin. This latter property allows investigators to better tune efficacy vs toxicity, and/or tissue specificity of the CAR T product, since lower-affinity binders may have higher specificity to tumors vs normal tissues due to higher expression of mesothelin on tumors than normal tissue, which may prevent on-target off tumor toxicity and bystander cell killing.

What follows is a detailed description of the inventive CARs including a description of their extracellular mesothelin antigen binding domain, the transmembrane domain and the intracellular domain, along with additional description of the CARs, antibodies and antigen binding fragments thereof, conjugates, nucleotides, expression, vectors, and host cells, methods of treatment, compositions, and kits employing the disclosed CARs.

A. Chimeric Antigen Receptors (CARs)

The CARs disclosed herein comprise at least one mesothelin antigen binding domain capable of binding to mesothelin, at least one transmembrane domain, and at least one intracellular domain.

A chimeric antigen receptor (CAR) is an artificially constructed hybrid protein or polypeptide containing the antigen binding domains of an antibody (e.g., single chain variable fragment (scFv)) linked to T-cell signaling domains via the transmembrane domain. Characteristics of CARs include their ability to redirect T-cell specificity and reactivity toward a selected target in a non-MHC-restricted manner, and exploiting the antigen-binding properties of monoclonal antibodies. The non-MHC-restricted antigen recognition gives T cells expressing CARS the ability to recognize antigen independent of antigen processing, thus bypassing a major mechanism of tumor escape. Moreover, when expressed in T-cells, CARS advantageously do not dimerize with endogenous T cell receptor (TCR) alpha and beta chains.

As disclosed herein, the intracellular T cell signaling domains of the CARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Domain

In one embodiment, the CAR comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in the CAR include those associated with viral, bacterial and parasitic infections, autoimmune disease and cancer cells.

In one embodiment, the CAR can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens include, for example, a glioma-associated antigen, carcinoembryonic antigen (CEA), .beta.-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

In one preferred embodiment, the tumor antigen is mesothelin and the tumors associated with expression of mesothelin comprise lung mesothelioma, ovarian, and pancreatic cancers that express high levels of the extracellular protein mesothelin, or any combination thereof.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSAs or TAAs include the following: Differentiation antigens such as MART-1/MelanA (MART-1), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In one embodiment, the antigen binding domain portion of the CAR targets an antigen that includes but is not limited to CD19, CD20, CD22, ROR1, CD33, c-Met, PSMA, Glycolipid F77, EGFRvIII, GD-2, MY-ESO-1 TCR, MAGE A3 TCR, and the like.

In a preferred embodiment, the antigen binding domain portion of the CAR targets the extracellular mesothelin antigen.

In one preferred embodiment, the isolated nucleic acid molecule encoding the extracellular mesothelin ScFv antigen binding domain comprises a nucleotide sequence of SEQ ID NO: 1, or a sequence with 85%, 90%, 95%, 96%, 97%, 98% or 99% identity thereof. In one embodiment, an isolated nucleic acid molecule is provided wherein the encoded extracellular mesothelin ScFv antigen binding domain comprises an amino acid sequence of SEQ ID NO: 2, or an amino acid sequence with 85%, 90%, 95%, 96%, 97%, 98% or 99% identity to an amino acid sequence of SEQ ID NO: 2.

In one preferred embodiment, the isolated nucleic acid molecule encoding the extracellular mesothelin ScFv antigen binding domain comprises a nucleotide sequence of SEQ ID NO: 3, or a sequence with 85%, 90%, 95%, 96%, 97%, 98% or 99% identity thereof. In one embodiment, an isolated nucleic acid molecule is provided wherein the encoded extracellular mesothelin ScFv antigen binding domain comprises an amino acid sequence of SEQ ID NO: 4, or an amino acid sequence with 85%, 90%, 95%, 96%, 97%, 98% or 99% identity to an amino acid sequence of SEQ ID NO: 4.

In one preferred embodiment, the isolated nucleic acid molecule encoding the extracellular mesothelin ScFv antigen binding domain comprises a nucleotide sequence of SEQ ID NO: 5, or a sequence with 85%, 90%, 95%, 96%, 97%, 98% or 99% identity thereof. In one embodiment, an isolated nucleic acid molecule is provided wherein the encoded extracellular mesothelin ScFv antigen binding domain comprises an amino acid sequence of SEQ ID NO: 6, or an amino acid sequence with 85%, 90%, 95%, 96%, 97%, 98% or 99% identity to an amino acid sequence of SEQ ID NO: 6.

In one preferred embodiment, the isolated nucleic acid molecule encoding the extracellular mesothelin ScFv antigen binding domain comprises a nucleotide sequence of SEQ ID NO: 7, or a sequence with 85%, 90%, 95%, 96%, 97%, 98% or 99% identity thereof. In one embodiment, an isolated nucleic acid molecule is provided wherein the encoded extracellular mesothelin ScFv antigen binding domain comprises an amino acid sequence of SEQ ID NO: 8, or an amino acid sequence with 85%, 90%, 95%, 96%, 97%, 98% or 99% identity to an amino acid sequence of SEQ ID NO: 8.

The generation and binding characteristics of the specific mesothelin ScFv antigen binding fragments or antigen binders described herein is shown in Example 1.

In the various embodiments of the mesothelin-specific CARS disclosed herein, the general scheme is set forth in FIG. 1 and includes, from the N-terminus to the C-terminus, a signal or leader peptide, anti-mesothelin scFv, extracellular linker, CD8 transmembrane, 4-1BB, CD3 zeta, wherein the bolded text represents the cloning sites for linking domains.

In one embodiment, the nucleic acid sequence encoding a CAR comprises the nucleic acid sequence of SEQ ID NO: 11, and encodes the CAR comprising the amino acid sequence as set forth in SEQ ID NO: 12 [pLTG1901:EF1a MH1P-CD8TM-4-1BB-CD3 zeta (pLTG1901)(as depicted in FIG. 2A)].

In one embodiment, the nucleic acid sequence encoding a CAR comprises the nucleic acid sequence of SEQ ID NO: 11, or a sequence with 85%, 90%, 95%, 96%, 97%, 98% or 99% identity thereof, and encodes the CAR comprising the amino acid sequence as set forth in SEQ ID NO: 12 or a sequence with 85%, 90%, 95%, 96%, 97%, 98% or 99% identity thereof [pLTG1901:EF1a MH1P-CD8TM-4-1BB-CD3 zeta (pLTG1901)(as depicted in FIG. 2A)].

In another embodiment, the nucleic acid sequence encoding a CAR comprises the nucleic acid sequence of SEQ ID NO: 13, and encodes the CAR comprising the amino acid sequence as set forth in SEQ ID NO: 14 [pLTG1902:Ef1a MH2P-CD8TM-4-1BB-CD3 zeta (pLTG1902) (as depicted in FIG. 2B)].

In another embodiment, the nucleic acid sequence encoding a CAR comprises the nucleic acid sequence of SEQ ID NO: 13 or a sequence with 85%, 90%, 95%, 96%, 97%, 98% or 99% identity thereof, and encodes the CAR comprising the amino acid sequence as set forth in SEQ ID NO: 14 or a sequence with 85%, 90%, 95%, 96%, 97%, 98% or 99% identity thereof [pLTG1902:Ef1a MH2P-CD8TM-4-1BB-CD3 zeta (pLTG1902) (as depicted in FIG. 2B)].

In another embodiment, the nucleic acid sequence encoding a CAR comprises the nucleic acid sequence of SEQ ID NO: 15, and encodes the CAR comprising the amino acid sequence as set forth in SEQ ID NO: 16 [pLTG1903:Ef1a-MH6P-CD8TM-4-1BB-CD3 zeta (pLTG1903) (as depicted in FIG. 2C)].

In another embodiment, the nucleic acid sequence encoding a CAR comprises the nucleic acid sequence of SEQ ID NO: 15 or a sequence with 85%, 90%, 95%, 96%, 97%, 98% or 99% identity thereof, and encodes the CAR comprising the amino acid sequence as set forth in SEQ ID NO: 16 or a sequence with 85%, 90%, 95%, 96%, 97%, 98% or 99% identity thereof [pLTG1903:Ef1a-MH6P-CD8TM-4-1BB-CD3 zeta (pLTG1903) (as depicted in FIG. 2C)].

In yet another embodiment, the nucleic acid sequence encoding a CAR comprises the nucleic acid sequence of SEQ ID NO: 17, and encodes the CAR comprising the amino acid sequence as set forth in SEQ ID NO: 18 [pLTG1904:Ef1a-M1-4S-CD8TM-4-1BB-CD3 zeta (pLTG1904) (as depicted in FIG. 2D)].

In yet another embodiment, the nucleic acid sequence encoding a CAR comprises the nucleic acid sequence of SEQ ID NO: 17 or a sequence with 85%, 90%, 95%, 96%, 97%, 98% or 99% identity thereof, and encodes the CAR comprising the amino acid sequence as set forth in SEQ ID NO: 18 or a sequence with 85%, 90%, 95%, 96%, 97%, 98% or 99% identity thereof [pLTG1904:Ef1a-M1-4S-CD8TM-4-1BB-CD3 zeta (pLTG1904) (as depicted in FIG. 2D)].

The surface expression of the mesothelin ScFv antigen binder-containing CARs is shown in Example 2 infra and summarized in Table 2. The expression level for each mesothelin ScFv antigen binder-containing CAR was determined by flow cytometric analysis of LV-transduced T cells from two healthy donors using the anti-human $F(ab')_2$ antibody fragment conjugated to phycoerythrin (PE) for CAR detection, (c.f., Example 2, FIG. 3). The anti-mesothelin CAR constructs 1901 and 1903 (solid traces) were not detected on T cell surface. By contrast, anti-mesothelin CARs 1902 and 1904 (solid traced) exhibited high surface expression compared to the GFP control construct (1398, shaded traces) which has no CAR T surface expression or cytolytic activity. Likewise, no CAR expression was detected in the negative control untransduced T cells (Mock group, not shown), further demonstrating the specificity of the detection method used. (c.f., Example 2, FIG. 3 and Table 2).

Figure 4:
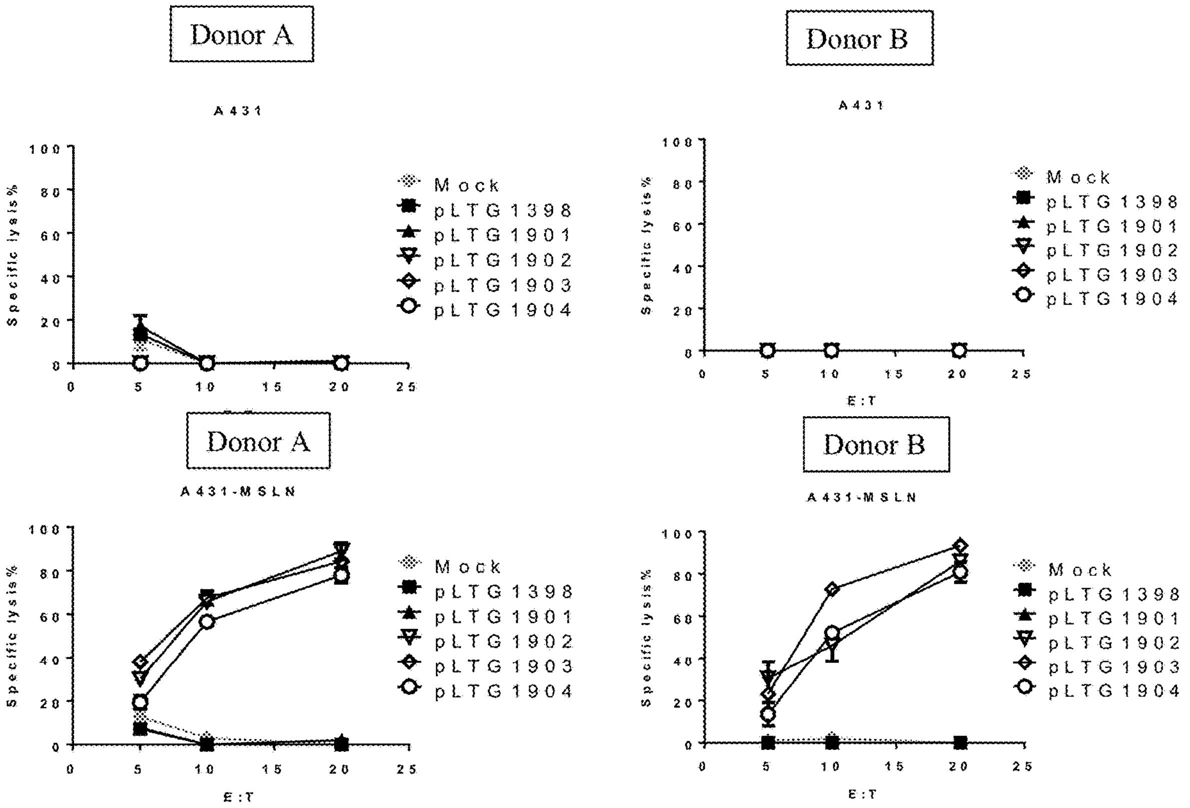
FIG. 4 depicts the anti-tumor activity of CARS containing the anti-mesothelin scFv binding motif, the CD8 transmembrane domain and the 4-1BB/CD3-zeta chain signaling motif. Anti-mesothelin CAR T cells were tested in an in vitro killing assay vs target lines stably expressing firefly luciferase. A431-mesothelin negative, A431-MSLN-mesothelin positive. CAR T cells were derived from blood of two healthy donors (Panels A and B). CART and tumor cells were combined in triplicates at the indicated effector to target (E:T) ratios and co-cultured overnight. Then, luminescence of surviving tumor cells in each well was assessed as described in Methods. Negative controls in this assay were pLTG1398-GFP and Mock-transduced T cells are negative controls. Bars represent Standard deviation for each group.

As shown in Example 2 and FIG. 4, respectively, the unexpected high cytolytic activity of the mesothelin scFv antigen binding domain-containing CARs was demonstrated when lentiviral vectors (LV) expressing the following CARs were created and tested for anti-leukemia activity. Each experimental CAR contains the 4-1BB/CD3-zeta chain signaling motif and the specific anti-mesothelin binding motif/domain noted therein. The A431-MSLN cell line was used as a target in cytolysis assays. Three of the CAR-T constructs featuring the anti-mesothelin binding ScFv connected in frame to CD8 linker and transmembrane regions and a 4-1BB/CD3-zeta chain signaling motif showed strong lytic activity at the effector to target (E:T) ratios listed on the x-axis (c.f, FIG. 4, pLTG1902 and pLTG1904, open triangle and circle, respectively). Surprisingly, strong cytolytic activity was seen with construct pLTG1903 (open diamond), although surface expression of this CAR construct could not be confirmed by flow cytometry. Furthermore, construct pLTG1901 (solid triangle), which also was undetectable on T cell surface by flow cytometry, exhibited no appreciable lytic activity (c.f., FIG. 4, pLTG1901, solid triangle), demonstrating that not all human-derived mesothelin scFv antigen binding domains behave similarly in the context of the CAR environment in which they are created.

Without being intended to limit to any particular mechanism of action, it is believed that possible reasons for the enhanced therapeutic function associated with the exemplary CARs of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or any combination thereof.

While the disclosure has been illustrated with as exemplary extracellular mesothelin scFv antigen binding domains, other nucleotide and/or amino acid variants within the mesothelin scFv antigen binding domains may be used to derive the mesothelin antigen binding domains for use in the CARs described herein.

Depending on the desired antigen to be targeted, the CAR can be additionally engineered to include the appropriate antigen bind domain that is specific to the desired antigen target. For example, if CD19 is the desired antigen that is to be targeted, an antibody for CD19 can be used as the antigen bind domain incorporation into the CAR.

In one exemplary embodiment, the antigen binding domain portion of the CAR additionally targets CD19. Preferably, the antigen binding domain in the CAR is anti-CD19 scFV, wherein the nucleic acid sequence of the anti-CD19 scFV comprises the sequence set forth in SEQ ID NO: 29 In one embodiment, the anti-CD19 scFV comprises the nucleic acid sequence that encodes the amino acid sequence of SEQ ID NO: 30. In another embodiment, the anti-CD19 scFV portion of the CAR comprises the amino acid sequence set forth in SEQ ID NO: 30.

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of *Staphylococci, Streptococcus, Escherichia coli, Pseudomonas*, or *Salmonella*. Particularly, there is provided a CAR capable of binding to an antigen derived from an infectious bacterium, for example, *Helicobacter pyloris, Legionella pneumophilia*, a bacterial strain of *Mycobacteria* sps. (e.g. *M. tuberculosis, M. avium, M. intracellulare, M. kansaii*, or *M. gordonea*), *Staphylococcus aureus, Neisseria gonorrhoeae, Neisseria meningitides, Listeria monocytogenes, Streptococcus pyogenes*, Group A *Streptococcus*, Group B *Streptococcus* (*Streptococcus agalactiae*), *Streptococcus pneumoniae*, or *Clostridium tetani*, or a combination thereof.

2. Transmembrane Domain

With respect to the transmembrane domain, the CAR comprises one or more transmembrane domains fused to the extracellular mesothelin antigen binding domain of the CAR.

The transmembrane domain may be derived either from a natural or from a synthetic source. Where the source is natural, the domain may be derived from any membrane-bound or transmembrane protein.

Transmembrane regions of particular use in the CARs described herein may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain that naturally is associated with one of the domains in the CAR is used in addition to the transmembrane domains described supra.

In some instances, the transmembrane domain can be selected or by amino acid substitution to avoid binding of such domains to the transmembrane domains of the same or different surface membrane proteins to minimize interactions with other members of the receptor complex.

In one embodiment, the transmembrane domain in the CAR of the invention is the CD8 transmembrane domain. In one embodiment, the CD8 transmembrane domain comprises the nucleic acid sequence of SEQ ID NO: 19. In one embodiment, the CD8 transmembrane domain comprises the nucleic acid sequence that encodes the amino acid sequence of SEQ ID NO: 20. In another embodiment, the CD8 transmembrane domain comprises the amino acid sequence of SEQ ID NO: 20.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO:20, or a sequence with 95-99% identity to an amino acid sequence of SEQ ID NO:20.

In some instances, the transmembrane domain of the CAR comprises the CD8.alpha.hinge domain. In one embodiment, the CD8 hinge domain comprises the nucleic acid sequence of SEQ ID NO: 21. In one embodiment, the CD8 hinge domain comprises the nucleic acid sequence that encodes the amino acid sequence of SEQ ID NO: 22. In another embodiment, the CD8 hinge domain comprises the amino acid sequence of SEQ ID NO: 22, or a sequence with 95-99% identify thereof.

In one embodiment, an isolated nucleic acid molecule is provided wherein the encoded linker domain is derived from the extracellular domain of CD8, and is linked to the transmembrane CD8 domain, the transmembrane CD28 domain, or a combination thereof.

3. Spacer Domain

In the CAR, a spacer domain can be arranged between the extracellular domain and the transmembrane domain, or between the intracellular domain and the transmembrane domain. The spacer domain means any oligopeptide or polypeptide that serves to link the transmembrane domain with the extracellular domain and/or the transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 79,645,667, 498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 118 to 178 (SEQ ID NO: 23) which is a hinge region of CD8.alpha. (NCBI RefSeq: NP.sub.-001759.3), amino acid numbers 135 to 195 of CD8.beta. (GenBank: AAA35664.1), amino acid numbers 315 to 396 of CD4 (NCBI RefSeq: NP.sub.-000607.1), or amino acid numbers 137 to 152 of CD28 (NCBI RefSeq: NP.sub.-006130.1) can be used. Also, as the spacer domain, a part of a constant region of an antibody H chain or L chain (CH1 region or CL region, for example, a peptide having an amino acid sequence shown in SEQ ID NO.: 24) can be used. Further, the spacer domain may be an artificially synthesized sequence.

Further, in the CAR, a signal peptide sequence can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the amino acid sequence shown in SEQ ID NO: 10).

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARS disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.-932170.1), amino acid numbers 45 to 86 of Fc.epsilon.RI.gamma. (NCBI RefSeq: NP.sub.-004097.1), amino acid numbers 201 to 244 of Fc.epsilon.RI.beta. (NCBI RefSeq: NP.sub.-000130.1), amino acid numbers 139 to 182 of CD3.gamma. (NCBI RefSeq: NP.sub.-000064.1), amino acid numbers 128 to 171 of CD3.delta. (NCBI RefSeq: NP.sub.-000723.1), amino acid numbers 153 to 207 of CD3. epsilon. (NCBI RefSeq: NP.sub.-000724.1), amino acid numbers 402 to 495 of CD5 (NCBI RefSeq: NP.sub.-055022.2), amino acid numbers 707 to 847 of 0022 (NCBI RefSeq: NP.sub.-001762.2), amino acid numbers 166 to 226 of CD79a (NCBI RefSeq: NP.sub.-001774.1), amino acid numbers 182 to 229 of CD79b (NCBI RefSeq: NP.sub.-000617.1), and amino acid numbers 177 to 252 of CD66d (NCBI RefSeq: NP.sub.-001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.-001758.2), amino acid numbers 421 to 458 of CD4 (NCBI RefSeq: NP.sub.-000607.1), amino acid numbers 402 to 495 of CD5 (NCBI RefSeq: NP.sub.-055022.2), amino acid numbers 207 to 235 of CD8.alpha. (NCBI RefSeq: NP.sub.-001759.3), amino acid numbers 196 to 210 of CD83 (GenBank: AAA35664.1), amino acid numbers 181 to 220 of CD28 (NCBI RefSeq: NP.sub.-006130.1), amino acid numbers 214 to 255 of CD137 (4-1BB, NCBI RefSeq: NP.sub.-001552.2), amino acid numbers 241 to 277 of CD134 (OX40, NCBI RefSeq: NP.sub.-003318.1), and amino acid numbers 166 to 199 of ICOS (NCBI RefSeq: NP.sub.-036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 25 and the signaling domain of CD3-zeta comprises the nucleic acid sequence set forth in SEQ ID NO: 27.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 26 and the signaling domain of CD3-zeta comprises the nucleic acid sequence that encodes the amino acid sequence of SEQ ID NO: 28.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 26 and the signaling domain of CD3-zeta comprises the amino acid sequence set forth in SEQ ID NO: 28.

5. Additional Description of CARs

Also expressly included within the scope of the invention are functional portions of the CARs disclosed herein. The term "functional portion" when used in reference to a CAR refers to any part or fragment of one or more of the CARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the CARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a non-polar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, 6-hydroxylysine, ornithine, -aminocyclopentane carboxylic acid, a-aminocyclohexane carboxylic acid, a-aminocycloheptane carboxylic acid, a-(2-amino-2-norbornane)-carboxylic acid, γ-diaminobutyric acid, β-diaminopropionic acid, homophenylalanine, and a-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, NY 2001; and Ausubel et al., Current Protocols in Molecular Biology, Greene Publishing Associates and John Wiley & Sons, NY, 1994. Further, some of the CARs (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the CARs can be synthetic, recombinant, isolated, and/or purified.

B. Antibodies and Antigen Binding Fragments

One embodiment further provides a CAR, a T cell expressing a CAR, an antibody, or antigen binding domain or portion thereof, which specifically binds to one or more of the antigens disclosed herein. As used herein, a "T cell expressing a CAR," or a "CAR T cell" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, 6.sup.th ed., W. H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, scFv, dsFv or Fab. References to "VL" or "VL" refer to the variable domain of an antibody light chain, including that of an Fv, scFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, MD, 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies; linear antibodies; single-chain antibody molecules (e.g. scFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (scFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a scFv, is typically not decisive for scFvs. Thus, scFvs with both possible arrangements (VH-domain-linker domain-VL-domain; VL-domain-linker domain-VH-domain) may be used.

In a dsFv the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holtiger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, IL); Kuby, J., Immunology, 3rd Ed., W. H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338, 929).

Also, a CAR, a T cell expressing a CAR, an antibody, or antigen binding portion thereof, can be to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

A CAR, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}I$, $^{32}P$, $^{14}C$, $^{3}H$ and $^{35}S$ and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine ($—NH_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, IL The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 79,645,667, 498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68: 92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include Pseudomonas exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, MO). Contemplated toxins also include variants of the toxins (see, for example, see, U.S. Pat. Nos. 5,079,163 and 4,689,401).

Saporin is a toxin derived from Saponaria officinalis that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from Corynebacterium diphtheriae. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from Micromonospora echinospora and are members of the enediyne antitumor antibiotic family that cause double strand breaks in DNA that lead to apoptosis (see, for example Lee et al., J. Antibiot. 42:1070-87, 1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

A CAR, a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, β-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the CARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, -carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-manosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, IA, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, MD), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA).

Bacteriophage vectors, such as λῠTIO, λῠTI 1, λZapII (Stratagene), EMBL4, and λNMI 149, also can be used. Examples of plant expression vectors include pBIO1, pBI101.2, pBHO1.3, pBI121 and pBIN19 (Clontech). Examples of animal expression vectors include pEUK-Cl, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include, for example, and not by way of limitation, the LENTIVECTOR® gene delivery technology from Oxford BioMedica plc, the LENTIMAX™ vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al, Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417 (1987)), and nucleic acid delivery using high velocity microprojectiles (see, e.g., Klein et al, Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupTl, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4+/CD8+ double positive T cells, CD4+ helper T cells, e.g., Thi and Th2 cells, CD8+ T cells (e.g., cytotoxic T cells), tumor infiltrating cells, memory T cells, na'ive T cells, and the like. The T cell may be a CD8+ T cell or a CD4+ T cell.

In an embodiment, the CARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

E. Methods of Treatment

It is contemplated that the CARs disclosed herein can be used in methods of treating or preventing a disease in a mammal. In this regard, an embodiment provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions in an amount effective to treat or prevent cancer in the mammal.

An embodiment further comprises lymphodepleting the mammal prior to administering the CARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., meduUoblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163: 507-513 (1999), teaches methods of measuring the release of cytokines (e.g., interferon-γ, granulocyte/monocyte colony stimulating factor (GM-CSF), tumor necrosis factor a (TNF-a) or interleukin 2 (IL-2)). In addition, CAR function can be evaluated by measurement of cellular cytotoxicity, as described in Zhao et al, J. Immunol, 174: 4415-4423 (2005).

Another embodiment provides for the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, CARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR-T cells, antibodies, antigen binding fragment, or conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masopro col, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Biopharmaceutical Compositions

Biopharmaceutical or biologics compositions (hereinafter, "compositions") are provided herein for use in gene therapy, immunotherapy and/or cell therapy that include one or more of the disclosed CARs, or T cells expressing a CAR, antibodies, antigen binding fragments, conjugates, CARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenus) or local (such as intra-tumor) administration. In one example, a disclosed CARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as *Remington's Pharmaceutical Science, 19th ed.*, Mack Publishing Company, Easton, PA (1995).

A CAR, or T cell expressing a CAR, antibodies, antigen binding fragments, or conjugates may be provided in lyophilized form and rehydrated with sterile water before administration, although they are also provided in sterile solutions of known concentration. The CARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, PA, (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, NY, pp. 219-342 (1994); and Tice & Tabibi, *Treatise on Controlled Drug Delivery*, A. Kydonieus, ed., Marcel Dekker, Inc. New York, NY, pp. 315-339, (1992).

Polymers can be used for ion-controlled release of the CARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, PA (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

G. Kits

In one aspect, kits employing the CARs disclosed herein are also provided. For example, kits for treating a tumor in a subject, or making a CAR T cell that expresses one or more of the CARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, CARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, CARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, CARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Identification of Mesothelin Antigen Binding Domains

Isolation of Mesothelin-Specific Antibodies from a Fully Human Phage-Displayed scFv Library Materials and Methods:

a) Production of Human Phage-Displayed scFv Mesothelin-Specific Antibodies

A naïve human scFv (recombinant single chain fragment variable of immunoglobulin) phage display library (approximate diversity, 1010 unique specificities), constructed from peripheral blood B cells of 50 healthy donors (Z. Y. Zhu and D. S. Dimitrov, unpublished data), was used for selection of scFvs specific for recombinant human mesothelin. Amplified libraries of 1012 phage-displayed scFv were incubated with 5, 3, and 1, μg of coated mesothelin in a 5×100-μl volume, distributed equally in 5 wells of a 96-well plate for 2 h at room temperature during the first, second and third rounds of biopanning, respectively. After each round of incubation the wells were washed 5 times for the first round and 10 times for the later rounds with phosphate-buffered saline containing 0.05% Tween 20 (PBST) to remove nonspecifically bound phage, the bound phage were mixed with TG1 competent cells for 1 hour at 37° C., and the phage was amplified from the infected cells and used in the next round of biopanning. After the third round of biopanning, 380 clones were randomly picked from the infected TG1 cells and each inoculated into 150 μl YT medium containing 100 μg/ml carbenicillin and 0.2% glucose in 96-well plates by using the automated BioRobotics BioPick colony picking system (Genomic Solutions, Ann Arbor, MI). After the bacterial cultures reached an optical density at 600 nm (OD600) of 0.5, helper phage M13K07 at a multiplicity of infection (MOI) of 10 and kanamycin at 50 μg/ml (final concentration) were added to the medium, and the plates were further incubated at 30° C. overnight in a shaker at 250 rpm. The phage supernatants were mixed with 3% nonfat milk in PBS at a 4:1 volume ratio and used for enzyme-linked immunosorbent assay (ELISA) to identify clones of phage displaying scFvs with high mesothelin binding affinity. The supernatants were incubated for 2 h at room temperature with recombinant human mesothelin coated at 50 ng per well in 96-well plates and washed five times with PBST, (after overnight incubation at 4° C. it was blocked with 3% nonfat milk in PBS and washed three times with PBS containing 0.05% Tween 20.) Mesothelin-bound phage were detected using horseradish peroxidase-conjugated goat anti-M13 antibody. After incubation with the antibody, the nonspecifically bound antibody was removed by washing wells, and the 3,3,'5,5'-tetramethylbenzidine (TMB) substrate was added, and solution absorbance at 450 nm (A450) measured. Clones that bound to mesothelin with A450 of >1.0 were selected for further characterization.

b) Expression and Purification of Selected Soluble scFvs.

The VH and VL of the selected clones were DNA sequenced, and the scFvs encoded by clones with unique sequences were expressed and purified as described below. Plasmids extracted from these clones were used for transformation of HB2151 cells. A single colony was picked from the plate containing freshly transformed cells, inoculated into 200 ml 2YT medium containing 100 μg/ml ampicillin and 0.2% glucose, and incubated at 37° C. with shaking at 250 rpm. When the culture OD at 600 nm reached 0.90, isopropyl-β-d-thiogalactopyranoside at a 0.5 mM final concentration was added, and the culture was further incubated overnight at 30° C. The bacterial pellet was collected after centrifugation at 8,000×g for 20 min and resuspended in PBS buffer containing 0.5 mU polymixin B (Sigma-Aldrich, St. Louis, MO). After 30 min incubation with rotation at 50 rpm at room temperature, the resuspended pellet was centrifuged at 25,000×g for 25 min at 4° C., and the supernatant was used for scFv purification using the Ni-NTA resin following vendor protocol (Qiagen).

c) ELISA Binding Assay

50 μl of the diluted recombinant human mesothelin in PBS at 2 ug/ml was coated in a 96-well plate at 4° C. overnight. Purified scFv (from above) with His and Flag tags was serially diluted and added into the target protein coated wells. After washing, a 1:3000 diluted HRP conjugated anti-Flag antibody was added for 1 hr at RT. After washing, 3,3,5,5'-Tetramethylbenzidine (TMB) substrate was added, 1N $H_2SO_4$ was added to stop the reaction after incubation at room temperature for 10 minutes, and the O.D. was read at 450 nm to quantify the relative ability of scFv to bind mesothelin.

Results:

Based upon the results of the ELISA binding assay, four separate scFs clones specific for recombinant human mesothelin were identified and labeled as human anti-mesothelin ScFv binders MH1P, MH2P, MH6P and M1-4S, respectively. The generation of chimeric antigen receptors expressing the MH1P, MH2P, MH6P and M1-4S human anti-mesothelin ScFv binders is outlined in Example 2, infra.

Example 2

CARs Expressing Anti-Mesothelin Fully Human ScFv Binding Sequences

In this Example, anti-mesothelin CAR T cells derived from four novel fully human ScFv binder sequences are described. The novel anti-mesothelin CART constructs have demonstrated high level expression in primary human T cells and specific and potent cytolytic activity against mesothelin-positive tumor cells.

Materials and Methods:

(a) Cell Lines

A431 human squamous carcinoma cell line was purchased from American Tissue Culture Collection (ATCC, Manassas, VA). The parent A431 line and its subclones were cultured in Dulbecco's Modified Eagle's Medium (ATCC) supplemented with 10% heat-inactivated fetal bovine serum.

Luciferase-expressing A431 subclone was generated by stably transducing wild-type A431 cells with lentiviral vector encoding firefly luciferase (Lentigen Technology, Inc., Gaithersburg, MD), followed by limiting dilution and selection of luciferase-positive clones. Similarly, A431-MSLN subclone was derived by transduction of A431 luciferase positive clone with a lentiviral vector encoding human mesothelin gene isoform 1 (RefSeq ID NM_005823.4), followed by selection of mesothelin positive clones.

(b) Creation of Chimeric Antigen Receptor (CAR)-Expression Vectors

CAR antigen-binding domains, scFv, sequences were derived from human anti-mesothelin ScFv binders MH1P, MH2P, MH6P and M1-4S. CAR T constructs were generated by linking binder scFv in frame to CD8a linking and transmembrane domains (UniProt sequence ID P01732, aa 138-206), and then to 4-1BB (CD137, aa 214-255, UniProt sequence ID Q07011) signaling domain and CD3 zeta signaling domain (CD247, aa 52-163, Ref sequence ID: NP_000725.1). CAR constructs sequences were cloned into a third generation lentiviral plasmid backbone (Lentigen Technology Inc., Gaithersburg, MD). Lentiviral vector (LV) containing supernatants were generated by transient transfection of HEK 293T cells and vector pelleted by centrifugation of lentiviral vector-containing supernatants, and stored at −80° C.

(c) Primary T Cell Purification and Transduction

Human primary T cells from normal donors were purified from buffy coats following immunomagnetic bead selection of CD4+ and CD8+ cells according to manufacturer's protocol (Miltenyi Biotec, Bergisch Gladbach, Germany), cultivated in TexMACS medium supplemented with 40 IU/ml IL-2 at a density of 0.3 to $2\times10^6$ cells/ml, activated with CD3/CD28 MACS® GMP TransAct reagent (Miltenyi Biotec) and transduced on day 3 with lentiviral vectors encoding CAR constructs in the presence of 10 ug/ml protamine sulfate (Sigma-Aldrich, St. Louis, MO) overnight, and media exchanged on day 4. On day 5, cultures were transferred to TexMACS medium supplemented with 200 IU/ml IL-2, and propagated until harvest on day 10-13.

(d) Immune Effector Assays (CTL and Cytokine)

To determine cell-mediated cytotoxicity (CTL assay), 5,000 target cells stably transduced with firefly luciferase were combined with CAR T cells at various effector to target ratios and incubated overnight. SteadyGlo reagent (Promega, Madison WI) was added to each well and the resulting luminescence quantified as counts per second (sample CPS). Target only wells (max CPS) and target only wells plus 1% Tween-20 (min CPS) were used to determine assay range. Percent specific lysis was calculated as: (1−(sample CPS−min CPS)/(max CPS−min CPS)).

(e) Flow Cytometric Analysis.

For cell staining, half a million CAR T transduced cells were harvested from culture, washed two times in cold AutoMACS buffer supplemented with 0.5% bovine serum albumin (Miltenyi Biotec), and CAR surface expression detected by staining with $F(ab')_2$ fragment-PE goat anti-human IgG reagent (Jackson ImmunoResearch Laboratories, West Grove, PA) at 1:200 dilution and incubation for 30 minutes at 4° C. Non-transduced cells were used as negative controls. Dead cells in all studies were excluded by 7AAD staining (BD Biosciences, San Jose, CA). Cells were washed twice and resuspended in 200 ul Staining Buffer before quantitative analysis by flow cytometry. Flow cytometric analysis was performed on a MACSQuant®10 Analyzer (Miltenyi Biotec), and data plots were generated using MACSQuantify software (Miltenyi Biotec).

Results:

In order to evaluate the novel anti-mesothelin fully human ScFv binding sequences, CAR constructs were designed incorporating each one of the sequences MH1P, MH2P, MH6P or M1-4S as a tumor antigen binding domain. In each CAR design, the tumor targeting domain was followed by a linker and transmembrane domains derived from the human CD8 protein, a 4-1BB costimulatory domain and a CD3 zeta signaling domain (Table 1).

TABLE 1

| List of Mesothelin - Targeting CAR Constructs |
|---|
| pLTG1901 EF1a MH1P-CD8TM-4-1BB-CD3 zeta |
| pLTG1902: Ef1a MH2P-CD8TM-4-1BB-CD3 zeta |
| pLTG1903: Ef1a-MH6P-CD8TM-4-1BB-CD3 zeta |
| pLTG1904: Ef1a-M1-4S-CD8TM-4-1BB-CD3 zeta |

T cells Transduced with Anti-Mesothelin Chimeric Antigen Receptors Demonstrate Surface Expression and Cytolytic Activity.

a) Surface Expression of Anti-Mesothelin CARs

To evaluate the four novel anti-mesothelin CARs, lentiviral vectors (LV) encoding CAR constructs MH1P, MH2P, MH6P and M1-4S under the control of human Ef1a promoter were generated as described in Materials and Methods. Then, human primary T cells derived from two separate healthy donors were transduced with the four lentiviral vectors encoding CARS. Non-transduced cells from same donor (Mock) or GFP-transduced cells from same donor served as negative controls.

T cells were activated on culture Day 0 with TransAct CD3 CD28 reagent in the presence of IL-2 as described in Materials and Methods. On culture Day 10, expression of anti-mesothelin CARS on T cell surface was detected by goat anti-human $F(ab')_2$-PE reagent and analyzed by flow cytometry. Anti-mesothelin CAR constructs pLTG1902 and pLTG1904 demonstrated high surface CAR expression. Unexpectedly, constructs pLTG1901 and pLTG1903 could not be detected on T cell surface by this method.

b) Cytolytic Assay of Anti-Mesothelin CARs

Figure 3:
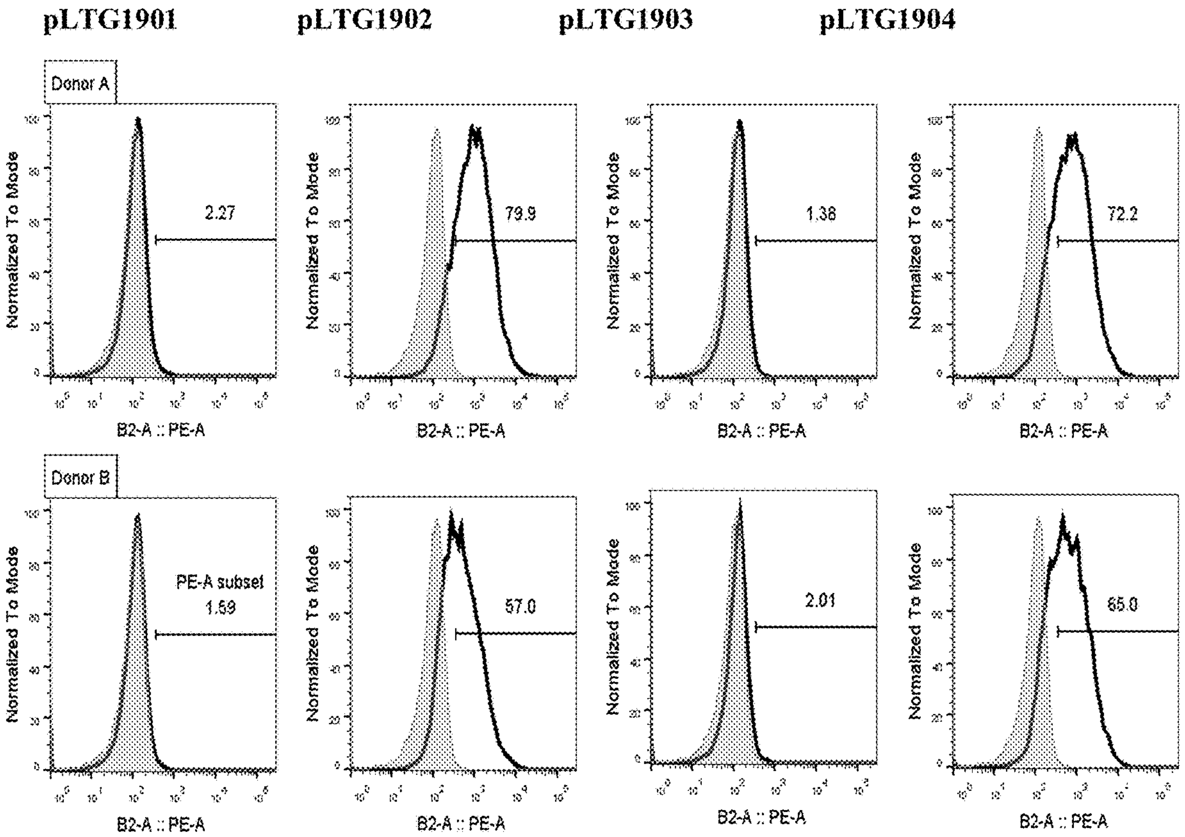
FIG. 3 depicts the expression of anti-mesothelin CAR in T cells. Primary human T cells derived from two healthy donors (A and B) were transduced with lentiviral vectors encoding the anti-mesothelin CAR constructs pLTG1901, pLTG1902, pLTG1903 and pLTG1904, respectively. Mock control constitutes T cells that were expanded in the absence of lentiviral transduction. On culture day 10, CAR surface expression was assessed by flow cytometry. Anti-human F(ab')2-PE reagent was used to facilitate the detection of anti-mesothelin CAR surface expression.

To demonstrate the cytolytic function of the generated CAR T cells, a luciferase-based killing assay was performed using A431-MSLN line stably expressing human mesothelin. The A431 parent line, which is mesothelin-negative, was used as a killing specificity control. CART cells and target cells were combined at effector to target (E:T) ratios of 20, 10 and 5, and co-incubated overnight, then cell killing was assessed by luminescence as described in Materials and Methods (FIG. 3). CAR T constructs pLTG1902, pLTG1903 and pLTG1904 showed strong, ratio-dependent cytotoxicity against A431-MSLN line, whereas the negative control GFP construct pLTG1398, and Mock (non-transduced T cells from same donor) were not cytolytic. Also, no cytolysis was observed in mesothelin-negative A431 line, indicating that the observed killing effect is mesothelin-specific. Notably, CAR pLTG1901 was not detected on T cell surface (FIG. 2) and showed no cytolytic activity against A431-MSLN cells. By contrast, CAR pLTG1903 which also could not be detected on T cell surface by flow cytometry, demonstrated strong cytotoxicity against A431-MSLN line, suggesting that this construct was also expressed in T cells. The result obtained with the CAR pLTG1903 demonstrated the unpredictability of correlation of cell surface expression with in vitro tumor cell killing ability.

In summary, high functionality of novel fully human anti-mesothelin CAR constructs pLTG1902, pLTG1903 and pLTG1904 (Table 2) was demonstrated. Construct pLTG1901 had no cytolytic effect, in concordance with lack of detectable surface expression by flow cytometry.

TABLE 2

Summary of Expression and Function - Anti-Mesothelin ScFv CARs

| Experimental Group | Expression | Cytolysis |
|---|---|---|
| Mock (untransduced control) | Undetected | None |
| pLTG1398 GFP | N/A/undetected | None |
| pLTG1901 CAR | Undetected | None |
| pLTG1902 CAR | High | High |
| pLTG1903 CAR | Undetected | High |
| pLTG1904 CAR | High | High |

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

REFERENCE TO THE SEQUENCE LISTING

This application contains a Sequence Listing electronically submitted to the United States Patent and Trademark Office via a PDF file entitled "Sequence Listing". The Sequence Listing is incorporated by reference.

SEQUENCES OF THE DISCLOSURE

The nucleic and amino acid sequences listed below are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

```
SEQ ID NO: 1 is the nucleotide sequence of mesothelin
antigen ScFv binding domain MH1P
caggtacagctgcagcagtcaggtccaggactggtgaagccctcgcggaccctc

tcactcacctgtgccatctccggggacagtgtctctagcaacagtgctgcttggaactgg

atcaggcagtccccatcgagaggccttgagtggctgggaaggacatactacaggtccaag

tggtataatgattatgcagtatctgtgaaaagtcgaataaccatcaacccagacacatcc

aagaaccagttctccctgcagctgaactctgtgactcccgaggacacggctgtgtattac

tgtgcaagagggaagggtggtaagaagggtggtgclittgatatctggggccaagggaca

atggtcaccgtctcttcaggaggtggcgggtctggtggaggcggtagcggcggtggcgga

tcctcttctgagctgactcaggaccctgctgtgtctgtggccttgggacagacagtcagg

atcacatgccaaggagacagcctcagaagctattatgcaagctggtaccagcagaagcca

ggacaggctcctgtacttgtcatctatggtaaaaacaaccggccctcagggatcccagac
```

-continued cgattctctggctcctcctcaggcaacacagcttccttgaccatcactggggctcaggcg gaagatgaggctgaatattactgtagctccagcactcgtaatcatgtgttcttcggcaga Gggaccaaggtcaccgtcctaggt SEQ ID NO: 2 is the amino acid sequence of mesothelin antigen ScFv binding domain MH1P

Q V Q L Q S G P G L V K P S R T L

S L T C A I S G D S V S S N S A A W N W

I R Q S P S R G L E W L G R T Y Y R S K

W Y N D Y A V S V K S R I T I N P D T S

K N Q F S L Q L N S V T P E D T A V Y Y

C A R G K G G K K G G A F D I W G Q G T

M V T V S S G G G G S G G G G S G G G G

S S S E L T Q D P A V S V A L G Q T V R

I T C Q G D S L R S Y Y A S W Y Q Q K P

G Q A P V L V I Y G K N N R P S G I P D

R F S G S S S G N T A S L T I T G A Q A

E D E A E Y Y C S S S T R N H V F F G R

G T K V T V L G

SEQ ID NO: 3 is the nucleotide sequence of mesothelin antigen ScFv binding domain MH2P gaggtgcagctggtgcagtctgggggaggcttggtacagcctggcaggtcccag agactctcctgtgcagcctctggattcacctttgatgattatgccatgcactgggtccgg caagctccagggaagggcctggagtgggtctcaggtattagttggaatagtggtagcata ggctatgcggactctgtgaagggccgattcaccatctccagagacaacgccaagaactcc ctgtatctgcaaatgaacagtctgagagctgaggacacggccttgtattactgtgcaaaa gatatttcgtcgtcagctggtaacgcttttgatatctggggccaagggacaatggtcacc gtctcttcaggaggtggcgggtctggtggaggcggtagcggcggtggcggatcctcttct gagctgactcaggaccctgctgtgtctgtggccttgggacagacagtcaggatcacatgc caaggagacagactcagaagctattatgcaagctggtaccagcagaagccaggacaggcc cctgtacttgtcatctatggtaaaaacaaccggccctcagggatcccagaccgcttctct ggctccgactcaggagacacagcttccttgaccatcactggggctcaggcggaagatgag gctgactattactgtcactcccgtgacagtggtggtaaccatgtggtattcggcggaggc Acccagctgaccgtcctcggt SEQ ID NO: 4 is the amino acid sequence of mesothelin antigen ScFv binding domain MH2P

E V Q L V Q S G G G L V Q P G R S Q

R L S C A A S G F T F D D Y A M H W V R

Q A P G K G L E W V S G I S W N S G S I

G Y A D S V K G R F T I S R D N A K N S

L Y L Q M N S L R A E D T A L Y Y C A K

D I S S S A G N A F D I W G Q G T M V T

V S S G G G G S G G G G S G G G G S S S

E L T Q D P A V S V A L G Q T V R I T C

-continued

Q G D R L R S Y Y A S W Y Q Q K P G Q A

P V L V I Y G K N N R P S G I P D R F S

G S D S G D T A S L T I T G A Q A E D E

A D Y Y C H S R D S G G N H V V F G G G

T Q L T V L G

SEQ ID NO: 5 is the nucleotide sequence of mesothelin antigen ScFv binding domain M1-4S
gaggtccagctggtacagtctgggggaggcttggtacagcctggggggtccctg agactctcctgtgcagcctctggattcacctttgatgattatgccatgcactgggtccgg caagctccagggaagggcctggagtgggtctcaggtattagttggaatagtggtagcata ggctatgcggactctgtgaagggccgattcaccatctccagagacaacgccaagaactcc ctgtatctgcaaatgaacagtctgagagctgaggacacggccttgtattactgtgcaaaa gatttatcgtcagtggctggaccctttaactactggggccagggcaccctggtcaccgtc tcctcaggaggtggcgggtctggtggaggcggtagcggcggtggcggatcctcttctgag ctgactcaggaccctgctgtgtctgtggccttgggacagacagtcaggatcacatgccaa ggagacagcctcagaagctattatgcaagctggtaccagcagaagccaggacaggcccct gtacttgtcatctatggtaaaaacaaccggccctcagggatcccagaccgattctctggc tccagctcaggaaacacagcttccttgaccatcactggggctcaggcggaggatgaggct gactattactgtaactcccgggacagcagtggtaaccatctggtattcggcggaggcacc Cagctgaccgtcctcggt SEQ ID NO: 6 is the amino acid sequence of mesothelin antigen ScFv binding domain M1-4S
E V Q L V Q S G G G L V Q P G G S L

R L S C A A S G F T F D D Y A M H W V R

Q A P G K G L E W V S G I S W N S G S I

G Y A D S V K G R F T I S R D N A K N S

L Y L Q M N S L R A E D T A L Y Y C A K

D L S S V A G P F N Y W G Q G T L V T V

S S G G G G S G G G G S G G G G S S S E

L T Q D P A V S V A L G Q T V R I T C Q

G D S L R S Y Y A S W Y Q Q K P G Q A P

V L V I Y G K N N R P S G I P D R F S G

S S S G N T A S L T I T G A Q A E D E A

D Y Y C N S R D S S G N H L V F G G G T

Q L T V L G

SEQ ID NO: 7 is the nucleotide sequence mesothelin antigen ScFv binding domain MH6P
caggtccagctggtgcagtctggggctgaggtgaagaagcctggggcctcagtg aaggtctcctgcaaggcttctggatacaccttcaccggctactatatgcactgggtgcga caggcccctggacaagggcttgagtggatgggacggatcaaccctaacagtggtggcaca aactatgcacagaagtttcagggcagggtcaccatgaccaggaacacgtccatcagcaca gcctacatggagctgagcaggctgagatctgacgacacggccgtgtattactgtgcgaga tccggctactactacggffiggacgtctggggccaagggaccacggtcaccgtctcctca ggaggtggcgggtctggtggaggcggtagcggcggtggcggatcccagtctgtgttgacg -continued cagccgccctcagcgtctgggacccccgggcagcgggtcaccatctcttgttctggaagt cgctccaacatcggaagaaacactgtcaactggtatcaacaactcccaggactggccccc aaactcatcatccagaggagtgatcagcggccctcaggggtccctgaccgattctctggc tccaagtctgtcacctcagcctccctggccatcagtgggctccggtccgaggatgaggct gattattactgcggaacatgggataacagcctgagtgcttatgtcttcggaactgggacc aagctgaccgtcctaggt SEQ ID NO: 8 is the amino acid sequence of mesothelin antigen ScFv binding domain MH6P

Q V Q L V Q S G A E V K K P G A S V

K V S C K A S G Y T F T G Y Y M H W V R

Q A P G Q G L E W M G R I N P N S G G T

N Y A Q K F Q G R V T M T R N T S I S T

A Y M E L S R L R S D D T A V Y Y C A R

S G Y Y Y G L D V W G Q G T T V T V S S

G G G G S G G G G S G G G G S Q S V L T

Q P P S A S G T P G Q R V T I S C S G S

R S N I G R N T V N W Y Q Q L P G L A P

K L I I Q R S D Q R P S G V P D R F S G

S K S V T S A S L A I S G L R S E D E A

D Y Y C G T W D N S L S A Y V F G T G T

K L T V L G

SEQ ID NO: 9 is the nucleotide sequence of leader/signal peptide sequence atgctgctgctggtgaccagcctgctgctgtgcgaactgccgcatccggcgtttctgctg attccg SEQ ID NO: 10 is the amino acid sequence of leader/signal peptide sequence

MLLLVTSLLLCELPHPAFLLIP

SEQ ID NO: 11 is the nucleotide sequence of pLTG1901 EF1a MH1P--CD8TM-4-1BB-CD3 zeta nucleic acid sequence

ATGCTGCTGCTGGTGACCAGCCTGCTGCTGTGCGAACTGCCGCATCCGGCGTTTCTGCTG

ATTCCGCAGGTACAGCTGCAGCAGTCAGGTCCAGGACTGGTGAAGCCCTCGCGGACCCTC

TCACTCACCTGTGCCATCTCCGGGGACAGTGTCTCTAGCAACAGTGCTGCTTGGAACTGG

ATCAGGCAGTCCCCATCGAGAGGCCTTGAGTGGCTGGGAAGGACATACTACAGGTCCAAG

TGGTATAATGATTATGCAGTATCTGTGAAAAGTCGAATAACCATCAACCCAGACACATCC

AAGAACCAGTTCTCCCTGCAGCTGAACTCTGTGACTCCCGAGGACACGGCTGTGTATTAC

TGTGCAAGAGGGAAGGGTGGTAAGAAGGGTGGTGCTTTTGATATCTGGGGCCAAGGGACA

ATGGTCACCGTCTCTTCAGGAGGTGGCGGGTCTGGTGGAGGCGGTAGCGGCGGTGGCGGA

TCCTCTTCTGAGCTGACTCAGGACCCTGCTGTGTCTGTGGCCTTGGGACAGACAGTCAGG

ATCACATGCCAAGGAGACAGCCTCAGAAGCTATTATGCAAGCTGGTACCAGCAGAAGCCA

GGACAGGCTCCTGTACTTGTCATCTATGGTAAAAACAACCGGCCCTCAGGGATCCCAGAC

CGATTCTCTGGCTCCTCCTCAGGCAACACAGCTTCCTTGACCATCACTGGGGCTCAGGCG

GAAGATGAGGCTGAATATTACTGTAGCTCCAGCACTCGTAATCATGTGTTCTTCGGCAGA

GGGACCAAGGTCACCGTCCTCGGTGCGGCCGCAACTACCACCCCTGCCCCTCGGCCGCCG

-continued

ACTCCGGCCCCAACCATCGCAAGCCAACCCCTCTCCTTGCGCCCCGAAGCTTGCCGCCCG

GCCGCGGGTGGAGCCGTGCATACCCGGGGGCTGGACTTTGCCTGCGATATCTACATTTGG

GCCCCGCTGGCCGGCACTTGCGGCGTGCTCCTGCTGTCGCTGGTCATCACCCTTTACTGC

AAGAGGGGCCGGAAGAAGCTGCTTTACATCTTCAAGCAGCCGTTCATGCGGCCCGTGCAG

ACGACTCAGGAAGAGGACGGATGCTCGTGCAGATTCCCTGAGGAGGAAGAGGGGGGATGC

GAACTGCGCGTCAAGTTCTCACGGTCCGCCGACGCCCCCGCATATCAACAGGGCCAGAAT

CAGCTCTACAACGAGCTGAACCTGGGAAGGAGAGAGGAGTACGACGTGCTGGACAAGCGA

CGCGGACGCGACCCGGAGATGGGGGGGAAACCACGGCGGAAAAACCCTCAGGAAGGACTG

TACAACGAACTCCAGAAAGACAAGATGGCGGAAGCCTACTCAGAAATCGGGATGAAGGGA

GAGCGGAGGAGGGGAAAGGGTCACGACGGGCTGTACCAGGGACTGAGCACCGCCACTAAG

GATACCTACGATGCCTTGCATATGCAAGCACTCCCACCCCGG

SEQ ID NO: 12 is the amino acid sequence of pLTG1901 EF1a MH1P--CD8TM-4-1BB-CD3 zeta amino acid sequence

MLLLVTSLLLCELPHPAFLLIPQVQLQQSGPGLVKPSRTLSLTCAISGDSVSSNSAAWNW

IRQSPSRGLEWLGRTYYRSKWYNDYAVSVKSRITINPDTSKNQFSLQLNSVTPEDTAVYY

CARGKGGKKGGAFDIWGQGTMVTVSSGGGGSGGGGSGGGGSSSELTQDPAVSVALGQTVR

ITCQGDSLRSYYASWYQQKPGQAPVLVIYGKNNRPSGIPDRFSGSSSGNTASLTITGAQA

EDEAEYYCSSSTRNHVFFGRGTKVTVLGAAATTTPAPRPPTPAPTIASQPLSLRPEACRP

AAGGAVHTRGLDFACDIYIWAPLAGTCGVLLLSLVITLYCKRGRKKLLYIFKQPFMRPVQ

TTQEEDGCSCRFPEEEEGGCELRVKFSRSADAPAYQQGQNQLYNELNLGRREEYDVLDKR

RGRDPEMGGKPRRKNPQEGLYNELQKDKMAEAYSEIGMKGERRRGKGHDGLYQGLSTATK

DTYDALHMQALPPR

SEQ ID NO: 13 is the nucleotide sequence of pLTG1902 Ef1a MH2P CD8TM-4-1BB-CD3 zeta nucleic acid sequence (FIG. 2B)

ATGCTGCTGCTGGTGACCAGCCTGCTGCTGTGCGAACTGCCGCATCCGGCGTTTCTGCTG

ATTCCGGAGGTGCAGCTGGTGCAGTCTGGGGGAGGCTTGGTACAGCCTGGCAGGTCCCAG

AGACTCTCCTGTGCAGCCTCTGGATTCACCTTTGATGATTATGCCATGCACTGGGTCCGG

CAAGCTCCAGGGAAGGGCCTGGAGTGGGTCTCAGGTATTAGTTGGAATAGTGGTAGCATA

GGCTATGCGGACTCTGTGAAGGGCCGATTCACCATCTCCAGAGACAACGCCAAGAACTCC

CTGTATCTGCAAATGAACAGTCTGAGAGCTGAGGACACGGCCTTGTATTACTGTGCAAAA

GATATTTCGTCGTCAGCTGGTAACGCTTTTGATATCTGGGGCCAAGGGACAATGGTCACC

GTCTCTTCAGGAGGTGGCGGGTCTGGTGGAGGCGGTAGCGGCGGTGGCGGATCCTCTTCT

GAGCTGACTCAGGACCCTGCTGTGTCTGTGGCCTTGGGACAGACAGTCAGGATCACATGC

CAAGGAGACAGACTCAGAAGCTATTATGCAAGCTGGTACCAGCAGAAGCCAGGACAGGCC

CCTGTACTTGTCATCTATGGTAAAAACAACCGGCCCTCAGGGATCCCAGACCGCTTCTCT

GGCTCCGACTCAGGAGACACAGCTTCCTTGACCATCACTGGGGCTCAGGCGGAAGATGAG

GCTGACTATTACTGTCACTCCCGTGACAGTGGTGGTAACCATGTGGTATTCGGCGGAGGC

ACCCAGCTGACCGTCCTCGGTGCGGCCGCAACTACCACCCCTGCCCCTCGGCCGCCGACT

CCGGCCCCAACCATCGCAAGCCAACCCCTCTCCTTGCGCCCCGAAGCTTGCCGCCCGGCC

GCGGGTGGAGCCGTGCATACCCGGGGGCTGGACTTTGCCTGCGATATCTACATTTGGGCC

CCGCTGGCCGGCACTTGCGGCGTGCTCCTGCTGTCGCTGGTCATCACCCTTTACTGCAAG

AGGGGCCGGAAGAAGCTGCTTTACATCTTCAAGCAGCCGTTCATGCGGCCCGTGCAGACG

ACTCAGGAAGAGGACGGATGCTCGTGCAGATTCCCTGAGGAGGAAGAGGGGGGATGCGAA

-continued

CTGCGCGTCAAGTTCTCACGGTCCGCCGACGCCCCCGCATATCAACAGGGCCAGAATCAG

CTCTACAACGAGCTGAACCTGGGAAGGAGAGAGGAGTACGACGTGCTGGACAAGCGACGC

GGACGCGACCCGGAGATGGGGGGGAAACCACGGCGGAAAAACCCTCAGGAAGGACTGTAC

AACGAACTCCAGAAAGACAAGATGGCGGAAGCCTACTCAGAAATCGGGATGAAGGGAGAG

CGGAGGAGGGGAAAGGGTCACGACGGGCTGTACCAGGGACTGAGCACCGCCACTAAGGAT

ACCTACGATGCCTTGCATATGCAAGCACTCCCACCCCGG

SEQ ID NO: 14 is the amino acid sequence of pLTG1902 Ef1a MH2P CD8TM-4-1BB-CD3 zeta amino acid sequence (FIG. 2B)

MLLLVTSLLLCELPHPAFLLIPEVQLVQSGGGLVQPGRSQRLSCAASGFTFDDYAMHWVR

QAPGKGLEWVSGISWNSGSIGYADSVKGRFTISRDNAKNSLYLQMNSLRAEDTALYYCAK

DISSSAGNAFDIWGQGTMVTVSSGGGGSGGGGSGGGGSSSELTQDPAVSVALGQTVRITC

QGDRLRSYYASWYQQKPGQAPVLVIYGKNNRPSGIPDRFSGSDSGDTASLTITGAQAEDE

ADYYCHSRDSGGNHVVFGGGTQLTVLGAAATTTPAPRPPTPAPTIASQPLSLRPEACRPA

AGGAVHTRGLDFACDIYIWAPLAGTCGVLLLSLVITLYCKRGRKKLLYIFKQPFMRPVQT

TQEEDGCSCRFPEEEEGGCELRVKFSRSADAPAYQQGQNQLYNELNLGRREEYDVLDKRR

GRDPEMGGKPRRKNPQEGLYNELQKDKMAEAYSEIGMKGERRRGKGHDGLYQGLSTATKD

TYDALHMQALPPR

SEQ ID NO. 15 is the nucleotide sequence of pLTG1903 Ef1a MH6P CD8TM-4-1BB-CD3 zeta nucleic acid sequence (FIG. 2C)

ATGCTGCTGCTGGTGACCAGCCTGCTGCTGTGCGAACTGCCGCATCCGGCGTTTCTGCTG

ATTCCGCAGGTCCAGCTGGTGCAGTCTGGGGCTGAGGTGAAGAAGCCTGGGGCCTCAGTG

AAGGTCTCCTGCAAGGCTTCTGGATACACCTTCACCGGCTACTATATGCACTGGGTGCGA

CAGGCCCCTGGACAAGGGCTTGAGTGGATGGGACGGATCAACCCTAACAGTGGTGGCACA

AACTATGCACAGAAGTTTCAGGGCAGGGTCACCATGACCAGGAACACGTCCATCAGCACA

GCCTACATGGAGCTGAGCAGGCTGAGATCTGACGACACGGCCGTGTATTACTGTGCGAGA

TCCGGCTACTACTACGGTTTGGACGTCTGGGGCCAAGGGACCACGGTCACCGTCTCCTCA

GGAGGTGGCGGGTCTGGTGGAGGCGGTAGCGGCGGTGGCGGATCCCAGTCTGTGTTGACG

CAGCCGCCCTCAGCGTCTGGGACCCCCGGGCAGCGGGTCACCATCTCTTGTTCTGGAAGT

CGCTCCAACATCGGAAGAAACACTGTCAACTGGTATCAACAACTCCCAGGACTGGCCCCC

AAACTCATCATCCAGAGGAGTGATCAGCGGCCCTCAGGGGTCCCTGACCGATTCTCTGGC

TCCAAGTCTGTCACCTCAGCCTCCCTGGCCATCAGTGGGCTCCGGTCCGAGGATGAGGCT

GATTATTACTGCGGAACATGGGATAACAGCCTGAGTGCTTATGTCTTCGGAACTGGGACC

AAGCTGACCGTCCTCGGTGCGGCCGCAACTACCACCCCTGCCCCTCGGCCGCCGACTCCG

GCCCCAACCATCGCAAGCCAACCCCTCTCCTTGCGCCCCGAAGCTTGCCGCCCGGCCGCG

GGTGGAGCCGTGCATACCCGGGGGCTGGACTTTGCCTGCGATATCTACATTTGGGCCCCG

CTGGCCGGCACTTGCGGCGTGCTCCTGCTGTCGCTGGTCATCACCCTTTACTGCAAGAGG

GGCCGGAAGAAGCTGCTTTACATCTTCAAGCAGCCGTTCATGCGGCCCGTGCAGACGACT

CAGGAAGAGGACGGATGCTCGTGCAGATTCCCTGAGGAGGAAGAGGGGGGATGCGAACTG

CGCGTCAAGTTCTCACGGTCCGCCGACGCCCCCGCATATCAACAGGGCCAGAATCAGCTC

TACAACGAGCTGAACCTGGGAAGGAGAGAGGAGTACGACGTGCTGGACAAGCGACGCGGA

CGCGACCCGGAGATGGGGGGGAAACCACGGCGGAAAAACCCTCAGGAAGGACTGTACAAC

GAACTCCAGAAAGACAAGATGGCGGAAGCCTACTCAGAAATCGGGATGAAGGGAGAGCGG

-continued

AGGAGGGGAAAGGGTCACGACGGGCTGTACCAGGGACTGAGCACCGCCACTAAGGATACC

TACGATGCCTTGCATATGCAAGCACTCCCACCCCGG

SEQ ID NO. 16 is the amino acid sequence of pLTG1903 Ef1a MH6P CD8TM-4-1BB-CD3 zeta amino acid sequence (FIG. 2C)

MLLLVTSLLLCELPHPAFLLIPQVQLVQSGAEVKKPGASVKVSCKASGYTFTGYYMHWVR

QAPGQGLEWMGRINPNSGGTNYAQKFQGRVTMTRNTSISTAYMELSRLRSDDTAVYYCAR

SGYYYGLDVWGQGTTVTVSSGGGGSGGGGSGGGGSQSVLTQPPSASGTPGQRVTISCSGS

RSNIGRNTVNWYQQLPGLAPKLIIQRSDQRPSGVPDRFSGSKSVTSASLAISGLRSEDEA

DYYCGTWDNSLSAYVFGTGTKLTVLGAAATTTPAPRPPTPAPTIASQPLSLRPEACRPAA

GGAVHTRGLDFACDIYIWAPLAGTCGVLLLSLVITLYCKRGRKKLLYIFKQPFMRPVQTT

QEEDGCSCRFPEEEEGGCELRVKFSRSADAPAYQQGQNQLYNELNLGRREEYDVLDKRRG

RDPEMGGKPRRKNPQEGLYNELQKDKMAEAYSEIGMKGERRRGKGHDGLYQGLSTATKDT

YDALHMQALPPR

SEQ ID NO. 17 is the nucleotide sequence of pLTG1904 Ef1a M1-4S CD8TM-4-1BB-CD3 zeta nucleic acid sequence (FIG. 2D)

ATGCTGCTGCTGGTGACCAGCCTGCTGCTGTGCGAACTGCCGCATCCGGCGTTTCTGCTG

ATTCCGGAGGTCCAGCTGGTACAGTCTGGGGGAGGCTTGGTACAGCCTGGGGGGTCCCTG

AGACTCTCCTGTGCAGCCTCTGGATTCACCTTTGATGATTATGCCATGCACTGGGTCCGG

CAAGCTCCAGGGAAGGGCCTGGAGTGGGTCTCAGGTATTAGTTGGAATAGTGGTAGCATA

GGCTATGCGGACTCTGTGAAGGGCCGATTCACCATCTCCAGAGACAACGCCAAGAACTCC

CTGTATCTGCAAATGAACAGTCTGAGAGCTGAGGACACGGCCTTGTATTACTGTGCAAAA

GATTTATCGTCAGTGGCTGGACCCTTTAACTACTGGGGCCAGGGCACCCTGGTCACCGTC

TCCTCAGGAGGTGGCGGGTCTGGTGGAGGCGGTAGCGGCGGTGGCGGATCCTCTTCTGAG

CTGACTCAGGACCCTGCTGTGTCTGTGGCCTTGGGACAGACAGTCAGGATCACATGCCAA

GGAGACAGCCTCAGAAGCTATTATGCAAGCTGGTACCAGCAGAAGCCAGGACAGGCCCCT

GTACTTGTCATCTATGGTAAAAACAACCGGCCCTCAGGGATCCCAGACCGATTCTCTGGC

TCCAGCTCAGGAAACACAGCTTCCTTGACCATCACTGGGGCTCAGGCGGAGGATGAGGCT

GACTATTACTGTAACTCCCGGGACAGCAGTGGTAACCATCTGGTATTCGGCGGAGGCACC

CAGCTGACCGTCCTCGGTGCGGCCGCAACTACCACCCCTGCCCCTCGGCCGCCGACTCCG

GCCCCAACCATCGCAAGCCAACCCCTCTCCTTGCGCCCCGAAGCTTGCCGCCCGGCCGCG

GGTGGAGCCGTGCATACCCGGGGGCTGGACTTTGCCTGCGATATCTACATTTGGGCCCCG

CTGGCCGGCACTTGCGGCGTGCTCCTGCTGTCGCTGGTCATCACCCTTTACTGCAAGAGG

GGCCGGAAGAAGCTGCTTTACATCTTCAAGCAGCCGTTCATGCGGCCCGTGCAGACGACT

CAGGAAGAGGACGGATGCTCGTGCAGATTCCCTGAGGAGGAAGAGGGGGGATGCGAACTG

CGCGTCAAGTTCTCACGGTCCGCCGACGCCCCCGCATATCAACAGGGCCAGAATCAGCTC

TACAACGAGCTGAACCTGGGAAGGAGAGAGGAGTACGACGTGCTGGACAAGCGACGCGGA

CGCGACCCGGAGATGGGGGGGAAACCACGGCGGAAAAACCCTCAGGAAGGACTGTACAAC

GAACTCCAGAAAGACAAGATGGCGGAAGCCTACTCAGAAATCGGGATGAAGGGAGAGCGG

AGGAGGGGAAAGGGTCACGACGGGCTGTACCAGGGACTGAGCACCGCCACTAAGGATACC

TACGATGCCTTGCATATGCAAGCACTCCCACCCCGG

-continued

SEQ ID NO: 18 is the amino acid sequence of pLTG1904 Ef1a M1-4S CD8TM-4-1BB-CD3 zeta amino acid sequence (FIG. 2D)
MLLLVTSLLLCELPHPAFLLIPEVQLVQSGGGLVQPGGSLRLSCAASGFTFDDYAMHWVR

QAPGKGLEWVSGISWNSGSIGYADSVKGRFTISRDNAKNSLYLQMNSLRAEDTALYYCAK

DLSSVAGPFNYWGQGTLVTVSSGGGGSGGGGSGGGGSSSELTQDPAVSVALGQTVRITCQ

GDSLRSYYASWYQQKPGQAPVLVIYGKNNRPSGIPDRFSGSSSGNTASLTITGAQAEDEA

DYYCNSRDSSGNHLVFGGGTQLTVLGAAATTTPAPRPPTPAPTIASQPLSLRPEACRPAA

GGAVHTRGLDFACDIYIWAPLAGTCGVLLLSLVITLYCKRGRKKLLYIFKQPFMRPVQTT

QEEDGCSCRFPEEEEGGCELRVKFSRSADAPAYQQGQNQLYNELNLGRREEYDVLDKRRG

RDPEMGGKPRRKNPQEGLYNELQKDKMAEAYSEIGMKGERRRGKGHDGLYQGLSTATKDT

YDALHMQALPPR

SEQ ID NO: 19 is the nucleotide sequence of DNA CD8 trans-membrane domain
atctacatct gggcgccctt ggccgggact tgtggggtcc ttctcctgtc actggttatc accctttact gc SEQ ID NO: 20 is the amino acid sequence of CD8 transmembrane domain
Ile Trp Ala Pro Leu Ala Gly Thr Cys Gly Val Leu Leu Leu Ser Leu Val Ile Thr Leu Tyr Cys SEQ ID NO: 21 is the nucleotide sequence of DNA CD8 hinge domain
accacgacgc cagcgccgcg accaccaaca ccggcgccca ccatcgcgtc gcagcccctg tccctgcgcc cagaggcgtg ccggccagcg gcggggggcg cagtgcacac gagggggctg gacttcgcct gtgat SEQ ID NO: 22 is the amino acid sequence of CD8 hinge domain
Thr Thr Thr Pro Ala Pro Arg Pro Pro Thr Pro Ala Pro Thr Ile Ala Ser Gln Pro Leu Ser Leu Arg Pro Glu Ala Cys Arg Pro Ala Ala Gly Gly Ala Val His Thr Arg Gly Leu Asp Phe Ala Cys Asp Ile Tyr SEQ ID NO: 23 is the amino acid sequence of amino acid numbers 118 to 178 hinge region of CD8.alpha. (NCBI RefSeq: NP.sub. --001759.3)
Lys Arg Gly Arg Lys Lys Leu Leu Tyr Ile Phe Lys Gln Pro Phe Met Arg Pro Val Gln Thr Thr Gln Glu Glu Asp Gly Cys Ser Cys Arg Phe Pro Glu Glu Glu Glu Gly Gly Cys Glu Leu SEQ ID NO: 24 is the amino acid sequence of Human IgG CL sequence
Gly Gln Pro Lys Ala Ala Pro Ser Val Thr Leu Phe Pro Pro Ser Ser Glu Glu Leu Gln Ala Asn Lys Ala Thr Leu Val Cys Leu Ile Ser Asp Phe Tyr Pro Gly Ala Val Thr Val Ala Trp Lys Ala Asp Ser Ser Pro Val Lys Ala Gly Val Glu Thr Thr Thr Pro Ser Lys Gln Ser Asn Asn Lys Tyr Ala Ala Ser Ser Tyr Leu Ser Leu Thr Pro Glu Gln Trp Lys Ser His Arg Ser Tyr Ser Cys Gln Val Thr His Glu Gly Ser Thr Val Glu Lys Thr Val Ala Pro Thr Glu Cys Ser SEQ ID NO: 25 is the nucleotide sequence of DNA signaling domain of 4-1BB
aaacggggca gaaagaaact cctgtatata ttcaaacaac catttatgag accagtacaa actactcaag aggaagatgg ctgtagctgc cgatttccag aagaagaaga aggaggatgt gaactg -continued SEQ ID NO: 26 is the amino acid sequence of signaling domain of 4-1BB
Lys Arg Gly Arg Lys Lys Leu Leu Tyr Ile Phe Lys Gln Pro Phe Met Arg Pro Val Gln Thr Thr Gln Glu Glu Asp Gly Cys Ser Cys Arg Phe Pro Glu Glu Glu Glu Gly Gly Cys Glu Leu SEQ ID NO: 27 is the nucleotide sequence of DNA signaling domain of CD3-zeta
agagtgaagt tcagcaggag cgcagacgcc cccgcgtaca agcagggcca gaaccagctc tataacgagc tcaatctagg acgaagagag gagtacgatg ttttggacaa gagacgtggc cgggaccctg agatgggggg aaagccgaga aggaagaacc ctcaggaagg cctgtacaat gaactgcaga aagataagat ggcggaggcc tacagtgaga ttgggatgaa aggcgagcgc cggaggggca aggggcacga tggcctttac cagggtctca gtacagccac caaggacacc tacgacgccc ttcacatgca ggccctgccc cctcgc SEQ ID NO: 28 is the amino acid sequence of CD3zeta
Arg Val Lys Phe Ser Arg Ser Ala Asp Ala Pro Ala Tyr Lys Gln Gly Gln Asn Gln Leu Tyr Asn Glu Leu Asn Leu Gly Arg Arg Glu Glu Tyr Asp Val Leu Asp Lys Arg Arg Gly Arg Asp Pro Glu Met Gly Gly Lys Pro Arg Arg Lys Asn Pro Gln Glu Gly Leu Tyr Asn Glu Leu Gln Lys Asp Lys Met Ala Glu Ala Tyr Ser Glu Ile Gly Met Lys Gly Glu Arg Arg Arg Gly Lys Gly His Asp Gly Leu Tyr Gln Gly Leu Ser Thr Ala Thr Lys Asp Thr Tyr Asp Ala Leu His Met Gln Ala Leu Pro Pro Arg SEQ ID NO: 29 is the nucleotide sequence of Scvf cd 19
gacatccaga tgacacagac tacatcctcc ctgtctgcct ctctgggaga cagagtcacc atcagttgca gggcaagtca ggacattagt aaatatttaa attggtatca gcagaaacca gatggaactg ttaaactcct gatctaccat acatcaagat tacactcagg agtcccatca aggttcagtg gcagtgggtc tggaacagat tattctctca ccattagcaa cctggagcaa gaagatattg ccacttactt ttgccaacag ggtaatacgc ttccgtacac gttcggaggg gggaccaagc tggagatcac aggtggcggt ggctcgggcg gtggtgggtc gggtggcggc ggatctgagg tgaaactgca ggagtcagga cctggcctgg tggcgccctc acagagcctg tccgtcacat gcactgtctc aggggtctca ttacccgact atggtgtaag ctggattcgc cagcctccac gaaagggtct ggagtggctg ggagtaatat ggggtagtga aaccacatac tataattcag ctctcaaatc cagactgacc atcatcaagg acaactccaa gagccaagtt ttcttaaaaa tgaacagtct gcaaactgat gacacagcca tttactactg tgccaaacat tattactacg gtggtagcta tgctatggac tactggggcc aaggaacctc agtcaccgtc tcctca SEQ ID NO: 30 is the amino acid sequence of Scvf cd 19
Asp Ile Gln Met Thr Gln Thr Thr Ser Ser Leu Ser Ala Ser Leu Gly Asp Arg Val Thr Ile Ser Cys Arg Ala Ser Gln Asp Ile Ser Lys Tyr Leu Asn Trp Tyr Gln Gln Lys Pro Asp Gly Thr Val Lys Leu Leu Ile Tyr His Thr Ser Arg Leu His Ser Gly Val Pro Ser Arg Phe Ser Gly Ser Gly Ser Gly Thr Asp Tyr Ser Leu Thr Ile Ser Asn Leu Glu Gln Glu Asp Ile Ala Thr Tyr Phe Cys Gln Gln Gly Asn Thr Leu Pro Tyr Thr Phe Gly Gly Gly Thr Lys Leu Glu Ile Thr Gly Gly Gly Gly Ser 100 105 110 Gly Gly Gly Gly Ser Gly Gly Gly Gly Ser Glu Val Lys -continued Leu Gln Glu Ser Gly Pro Gly Leu Val Ala Pro Ser Gln Ser Leu Ser Val Thr Cys Thr Val Ser Gly Val Ser Leu Pro Asp Tyr Gly Val Ser Trp Ile Arg Gln Pro Pro Arg Lys Gly Leu Glu Trp Leu Gly Val Ile Trp Gly Ser Glu Thr Thr Tyr Tyr Asn Ser Ala Leu Lys Ser Arg Leu Thr Ile Ile Lys Asp Asn Ser Lys Ser Gln Val Phe Leu Lys Met Asn Ser Leu Gln Thr Asp Asp Thr Ala Ile Tyr Tyr Cys Ala Lys His Tyr Tyr Tyr Gly Gly Ser Tyr Ala Met Asp Tyr Trp Gly Gln Gly Thr Ser Val Thr Val Ser Ser

What is claimed is:

1. A method of providing an anti-tumor immunity in a human subject having a tumor comprising administering to the human subject having the tumor an effective amount of an isolated T cell or an isolated natural killer (NK) cell, wherein the isolated T cell or the isolated NK cell comprises a vector comprising a nucleic acid molecule encoding a chimeric antigen receptor (CAR) comprising at least one extracellular antigen binding domain comprising a mesothelin antigen binding domain comprising the amino acid sequence of SEQ ID NO. 4, 6, or 8, at least one linker or spacer domain, at least one transmembrane domain, and at least one intracellular signaling domain, thereby providing anti-tumor immunity to the human subject having the tumor.

2. The method of claim 1, wherein the at least one transmembrane domain comprises a transmembrane domain of a protein selected from the group consisting of: the alpha chain of a T-cell receptor, the beta chain of a T-cell receptor, the zeta chain of a T-cell receptor, CD8, CD28, CD3 epsilon, CD45, CD4, CD5, CD9, CD16, CD22, CD33, CD37, CD64, CD80, CD86, CD134, CD137, and CD154.

3. The method of claim 1, wherein the encoded at least one mesothelin antigen binding domain, the at least one intracellular signaling domain, or both are connected to the at least one transmembrane domain by the at least one linker or spacer domain.

4. The method of claim 3, wherein the encoded at least one linker or spacer domain is from the extracellular domain of CD8 or CD28, and is linked to the at least one transmembrane domain.

5. The method of claim 1, wherein the nucleic acid sequence encoding the mesothelin antigen binding domain comprises a nucleic acid sequence comprising SEQ ID NO, 3, 5, or 7, or a sequence with 85%, 90%, 95%, 96%, 97%, 98% or 99% identity thereof.

6. The method of claim 1, wherein the encoded at least one intracellular signaling domain comprises a signaling domain of CD3 zeta.

7. The method of claim 1, wherein the encoded at least one intracellular signaling domain comprises a costimulatory domain, a primary signaling domain, or a costimulatory domain and a primary signaling domain.

8. The method of claim 7, wherein the costimulatory domain comprises a functional signaling domain of a protein selected from the group consisting of: OX40, CD70, CD27, CD28, CD5, ICAM-1, LFA-1 (CD11a/CD18), ICOS (CD278), DAP10, DAP12, and 4-1BB (CD137).

9. The method of claim 1, wherein the CAR comprises SEQ ID NO: 14, SEQ ID NO: 16, or SEQ ID NO: 18.

10. A method of treating cancer in a human subject, comprising administering to the human subject an effective amount of an isolated T cell or an isolated NK cell, wherein the isolated T cell or the isolated NK cell comprises a vector comprising a nucleic acid molecule encoding a CAR comprising at least one extracellular antigen binding domain comprising a mesothelin antigen binding domain comprising the amino acid sequence of SEQ ID NO. 4, 6, or 8, at least one linker or spacer domain, at least one transmembrane domain, and at least one intracellular signaling domain, to treat cancer in the human subject.

11. The method of claim 10, wherein the at least one transmembrane domain comprises a transmembrane domain of a protein selected from the group consisting of: the alpha chain of a T-cell receptor, the beta chain of a T-cell receptor, the zeta chain of a T-cell receptor, CD8, CD28, CD3 epsilon, CD45, CD4, CD5, CD9, CD16, CD22, CD33, CD37, CD64, CD80, CD86, CD134, CD137, and CD154.

12. The method of claim 10, wherein the encoded at least one mesothelin antigen binding domain, the at least one intracellular signaling domain, or both are connected to the at least one transmembrane domain by the at least one linker or spacer domain.

13. The method of claim 12, wherein the encoded at least one linker or spacer domain is from the extracellular domain of CD8 or CD28, and is linked to the at least one transmembrane domain.

14. The method of claim 10, wherein the nucleic acid sequence encoding the mesothelin antigen binding domain comprises a nucleic acid sequence comprising SEQ ID NO, 3, 5, or 7, or a sequence with 85%, 90%, 95%, 96%, 97%, 98% or 99% identity thereof.

15. The method of claim 10, wherein the encoded at least one intracellular signaling domain comprises a signaling domain of CD3 zeta.

16. The method of claim 10, wherein the encoded at least one intracellular signaling domain comprises a costimulatory domain, a primary signaling domain, or a costimulatory domain and a primary signaling domain.

17. The method of claim 16, wherein the costimulatory domain comprises a functional signaling domain of a protein selected from the group consisting of: OX40, CD70, CD27, CD28, CD5, ICAM-1, LFA-1 (CD11a/CD18), ICOS (CD278), DAP10, DAP12, and 4-1BB (CD137).

18. The method of claim 10, wherein the CAR comprises SEQ ID NO: 14, SEQ ID NO: 16, or SEQ ID NO: 18.

* * * * *

SEQUENCE LISTING

<160> NUMBER OF SEQ ID NOS: 30

<210> SEQ ID NO 1
<211> LENGTH: 738
<212> TYPE: DNA
<213> ORGANISM: Artificial Sequence
<220> FEATURE:
<223> OTHER INFORMATION: mesothelin antigen ScFv binding domain MH1P

<400> SEQUENCE: 1
caggtacagc tgcagcagtc aggtccagga ctggtgaagc cctcgcggac cctctcactc 60
acctgtgcca tctccgggga cagtgtctct agcaacagtg ctgcttggaa ctggatcagg 120
cagtccccat cgagaggcct tgagtggctg ggaaggacat actacaggtc caagtggtat 180
aatgattatg cagtatctgt gaaaagtcga ataaccatca acccagacac atccaagaac 240
cagttctccc tgcagctgaa ctctgtgact cccgaggaca cggctgtgta ttactgtgca 300
agagggaagg gtggtaagaa gggtggtgct tttgatatct ggggccaagg gacaatggtc 360
accgtctctt caggaggtgg cgggtctggt ggaggcggta gcggcggtgg cggatcctct 420
tctgagctga ctcaggaccc tgctgtgtct gtggccttgg gacagacagt caggatcaca 480
tgccaaggag acagcctcag aagctattat gcaagctggt accagcagaa gccaggacag 540
gctcctgtac ttgtcatcta tggtaaaaac aaccggccct cagggatccc agaccgattc 600
tctggctcct cctcaggcaa cacagcttcc ttgaccatca ctggggctca ggcggaagat 660
gaggctgaat attactgtag ctccagcact cgtaatcatg tgttcttcgg cagagggacc 720
aaggtcaccg tcctaggt 738

<210> SEQ ID NO 2
<211> LENGTH: 245
<212> TYPE: PRT
<213> ORGANISM: Artificial Sequence
<220> FEATURE:
<223> OTHER INFORMATION: mesothelin antigen ScFv binding domain MH1P

<400> SEQUENCE: 2

Gln Val Gln Leu Gln Ser Gly Pro Gly Leu Val Lys Pro Ser Arg Thr
1 5 10 15

Leu Ser Leu Thr Cys Ala Ile Ser Gly Asp Ser Val Ser Ser Asn Ser
20 25 30

Ala Ala Trp Asn Trp Ile Arg Gln Ser Pro Ser Arg Gly Leu Glu Trp
35 40 45

Leu Gly Arg Thr Tyr Tyr Arg Ser Lys Trp Tyr Asn Asp Tyr Ala Val
50 55 60

```
Ser Val Lys Ser Arg Ile Thr Ile Asn Pro Asp Thr Ser Lys Asn Gln
65                  70                  75                  80

Phe Ser Leu Gln Leu Asn Ser Val Thr Pro Glu Asp Thr Ala Val Tyr
                85                  90                  95

Tyr Cys Ala Arg Gly Lys Gly Gly Lys Lys Gly Gly Ala Phe Asp Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Gly Ser Ser Ser Glu Leu Thr Gln
    130                 135                 140

Asp Pro Ala Val Ser Val Ala Leu Gly Gln Thr Val Arg Ile Thr Cys
145                 150                 155                 160

Gln Gly Asp Ser Leu Arg Ser Tyr Tyr Ala Ser Trp Tyr Gln Gln Lys
                165                 170                 175

Pro Gly Gln Ala Pro Val Leu Val Ile Tyr Gly Lys Asn Asn Arg Pro
            180                 185                 190

Ser Gly Ile Pro Asp Arg Phe Ser Gly Ser Ser Ser Gly Asn Thr Ala
        195                 200                 205

Ser Leu Thr Ile Thr Gly Ala Gln Ala Glu Asp Glu Ala Glu Tyr Tyr
    210                 215                 220

Cys Ser Ser Ser Thr Arg Asn His Val Phe Phe Gly Arg Gly Thr Lys
225                 230                 235                 240

Val Thr Val Leu Gly
                245


<210> SEQ ID NO 3
<211> LENGTH: 735
<212> TYPE: DNA
<213> ORGANISM: Artificial Sequence
<220> FEATURE:
<223> OTHER INFORMATION: mesothelin antigen ScFv binding domain MH2P

<400> SEQUENCE: 3

gaggtgcagc tggtgcagtc tgggggaggc ttggtacagc ctggcaggtc ccagagactc      60

tcctgtgcag cctctggatt cacctttgat gattatgcca tgcactgggt ccggcaagct     120

ccagggaagg gcctggagtg ggtctcaggt attagttgga atagtggtag cataggctat     180

gcggactctg tgaagggccg attcaccatc tccagagaca acgccaagaa ctccctgtat     240

ctgcaaatga acagtctgag agctgaggac acggccttgt attactgtgc aaaagatatt     300

tcgtcgtcag ctggtaacgc ttttgatatc tggggccaag ggacaatggt caccgtctct     360

tcaggaggtg gcgggtctgg tggaggcggt agcggcggtg gcggatcctc ttctgagctg     420

actcaggacc ctgctgtgtc tgtggccttg ggacagacag tcaggatcac atgccaagga     480

gacagactca gaagctatta tgcaagctgg taccagcaga agccaggaca ggcccctgta     540

cttgtcatct atggtaaaaa caaccggccc tcagggatcc cagaccgctt ctctggctcc     600

gactcaggag acacagcttc cttgaccatc actggggctc aggcggaaga tgaggctgac     660

tattactgtc actcccgtga cagtggtggt aaccatgtgg tattcggcgg aggcacccag     720

ctgaccgtcc tcggt                                                      735


<210> SEQ ID NO 4
<211> LENGTH: 245
<212> TYPE: PRT
<213> ORGANISM: Artificial Sequence
<220> FEATURE:
```

<223> OTHER INFORMATION: mesothelin antigen ScFv binding domain MH2P

<400> SEQUENCE: 4

```
Glu Val Gln Leu Val Gln Ser Gly Gly Gly Leu Val Gln Pro Gly Arg
1               5                   10                  15

Ser Gln Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Ser Ser Ser Ala Gly Asn Ala Phe Asp Ile Trp Gly
            100                 105                 110

Gln Gly Thr Met Val Thr Val Ser Ser Gly Gly Gly Gly Ser Gly Gly
        115                 120                 125

Gly Gly Ser Gly Gly Gly Gly Ser Ser Ser Glu Leu Thr Gln Asp Pro
    130                 135                 140

Ala Val Ser Val Ala Leu Gly Gln Thr Val Arg Ile Thr Cys Gln Gly
145                 150                 155                 160

Asp Arg Leu Arg Ser Tyr Tyr Ala Ser Trp Tyr Gln Gln Lys Pro Gly
                165                 170                 175

Gln Ala Pro Val Leu Val Ile Tyr Gly Lys Asn Asn Arg Pro Ser Gly
            180                 185                 190

Ile Pro Asp Arg Phe Ser Gly Ser Asp Ser Gly Asp Thr Ala Ser Leu
        195                 200                 205

Thr Ile Thr Gly Ala Gln Ala Glu Asp Glu Ala Asp Tyr Tyr Cys His
    210                 215                 220

Ser Arg Asp Ser Gly Gly Asn His Val Val Phe Gly Gly Gly Thr Gln
225                 230                 235                 240

Leu Thr Val Leu Gly
                245
```

<210> SEQ ID NO 5
<211> LENGTH: 732
<212> TYPE: DNA
<213> ORGANISM: Artificial Sequence
<220> FEATURE:
<223> OTHER INFORMATION: mesothelin antigen ScFv binding domain M1-4S

<400> SEQUENCE: 5

```
gaggtccagc tggtacagtc tgggggaggc ttggtacagc ctggggggtc cctgagactc      60

tcctgtgcag cctctggatt cacctttgat gattatgcca tgcactgggt ccggcaagct     120

ccagggaagg gcctggagtg ggtctcaggt attagttgga atagtggtag cataggctat     180

gcggactctg tgaagggccg attcaccatc tccagagaca acgccaagaa ctccctgtat     240

ctgcaaatga acagtctgag agctgaggac acggccttgt attactgtgc aaaagattta     300

tcgtcagtgg ctggaccctt taactactgg ggccagggca ccctggtcac cgtctcctca     360

ggaggtggcg ggtctggtgg aggcggtagc ggcggtggcg gatcctcttc tgagctgact     420

caggaccctg ctgtgtctgt ggccttggga cagacagtca ggatcacatg ccaaggagac     480

agcctcagaa gctattatgc aagctggtac cagcagaagc caggacaggc ccctgtactt     540
```

-continued gtcatctatg gtaaaaacaa ccggccctca gggatcccag accgattctc tggctccagc 600
tcaggaaaca cagcttcctt gaccatcact ggggctcagg cggaggatga ggctgactat 660
tactgtaact cccgggacag cagtggtaac catctggtat tcggcggagg cacccagctg 720
accgtcctcg gt 732

<210> SEQ ID NO 6
<211> LENGTH: 244
<212> TYPE: PRT
<213> ORGANISM: Artificial Sequence
<220> FEATURE:
<223> OTHER INFORMATION: mesothelin antigen ScFv binding domain M1-4S

<400> SEQUENCE: 6

Glu Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Ile Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Lys Asp Leu Ser Ser Val Ala Gly Pro Phe Asn Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Ser Ser Glu Leu Thr Gln Asp Pro Ala
130 135 140

Val Ser Val Ala Leu Gly Gln Thr Val Arg Ile Thr Cys Gln Gly Asp
145 150 155 160

Ser Leu Arg Ser Tyr Tyr Ala Ser Trp Tyr Gln Gln Lys Pro Gly Gln
165 170 175

Ala Pro Val Leu Val Ile Tyr Gly Lys Asn Asn Arg Pro Ser Gly Ile
180 185 190

Pro Asp Arg Phe Ser Gly Ser Ser Ser Gly Asn Thr Ala Ser Leu Thr
195 200 205

Ile Thr Gly Ala Gln Ala Glu Asp Glu Ala Asp Tyr Tyr Cys Asn Ser
210 215 220

Arg Asp Ser Ser Gly Asn His Leu Val Phe Gly Gly Gly Thr Gln Leu
225 230 235 240

Thr Val Leu Gly

<210> SEQ ID NO 7
<211> LENGTH: 732
<212> TYPE: DNA
<213> ORGANISM: Artificial Sequence
<220> FEATURE:
<223> OTHER INFORMATION: mesothelin antigen ScFv binding domain MH6P

<400> SEQUENCE: 7
caggtccagc tggtgcagtc tggggctgag gtgaagaagc ctggggcctc agtgaaggtc 60
tcctgcaagg cttctggata caccttcacc ggctactata tgcactgggt gcgacaggcc 120

```
cctggacaag ggcttgagtg gatgggacgg atcaacccta acagtggtgg cacaaactat    180

gcacagaagt ttcagggcag ggtcaccatg accaggaaca cgtccatcag cacagcctac    240

atggagctga gcaggctgag atctgacgac acggccgtgt attactgtgc gagatccggc    300

tactactacg gtttggacgt ctggggccaa gggaccacgg tcaccgtctc ctcaggaggt    360

ggcgggtctg gtggaggcgg tagcggcggt ggcggatccc agtctgtgtt gacgcagccg    420

ccctcagcgt ctgggacccc cgggcagcgg gtcaccatct cttgttctgg aagtcgctcc    480

aacatcggaa gaaacactgt caactggtat caacaactcc caggactggc ccccaaactc    540

atcatccaga ggagtgatca gcggccctca ggggtccctg accgattctc tggctccaag    600

tctgtcacct cagcctccct ggccatcagt gggctccggt ccgaggatga ggctgattat    660

tactgcggaa catgggataa cagcctgagt gcttatgtct tcggaactgg gaccaagctg    720

accgtcctag gt                                                        732


<210> SEQ ID NO 8
<211> LENGTH: 244
<212> TYPE: PRT
<213> ORGANISM: Artificial Sequence
<220> FEATURE:
<223> OTHER INFORMATION: mesothelin antigen ScFv binding domain MH6P

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Tyr Tyr Tyr Gly Leu Asp Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gln Ser Val Leu Thr Gln Pro Pro Ser Ala Ser
    130                 135                 140

Gly Thr Pro Gly Gln Arg Val Thr Ile Ser Cys Ser Gly Ser Arg Ser
145                 150                 155                 160

Asn Ile Gly Arg Asn Thr Val Asn Trp Tyr Gln Gln Leu Pro Gly Leu
                165                 170                 175

Ala Pro Lys Leu Ile Ile Gln Arg Ser Asp Gln Arg Pro Ser Gly Val
            180                 185                 190

Pro Asp Arg Phe Ser Gly Ser Lys Ser Val Thr Ser Ala Ser Leu Ala
        195                 200                 205

Ile Ser Gly Leu Arg Ser Glu Asp Glu Ala Asp Tyr Tyr Cys Gly Thr
    210                 215                 220

Trp Asp Asn Ser Leu Ser Ala Tyr Val Phe Gly Thr Gly Thr Lys Leu
225                 230                 235                 240

Thr Val Leu Gly
```

<210> SEQ ID NO 9
<211> LENGTH: 66
<212> TYPE: DNA
<213> ORGANISM: Artificial Sequence
<220> FEATURE:
<223> OTHER INFORMATION: leader/signal peptide sequence

<400> SEQUENCE: 9
atgctgctgc tggtgaccag cctgctgctg tgcgaactgc cgcatccggc gtttctgctg 60
attccg 66

<210> SEQ ID NO 10
<211> LENGTH: 22
<212> TYPE: PRT
<213> ORGANISM: Artificial Sequence
<220> FEATURE:
<223> OTHER INFORMATION: leader/signal peptide sequence

<400> SEQUENCE: 10

Met Leu Leu Leu Val Thr Ser Leu Leu Leu Cys Glu Leu Pro His Pro
1 5 10 15

Ala Phe Leu Leu Ile Pro
20

<210> SEQ ID NO 11
<211> LENGTH: 1482
<212> TYPE: DNA
<213> ORGANISM: Artificial Sequence
<220> FEATURE:
<223> OTHER INFORMATION: pLTG1901 EF1a MH1P--CD8TM-4-1BB-CD3 zeta

<400> SEQUENCE: 11
atgctgctgc tggtgaccag cctgctgctg tgcgaactgc cgcatccggc gtttctgctg 60
attccgcagg tacagctgca gcagtcaggt ccaggactgg tgaagccctc gcggaccctc 120
tcactcacct gtgccatctc cggggacagt gtctctagca acagtgctgc ttggaactgg 180
atcaggcagt ccccatcgag aggccttgag tggctgggaa ggacatacta caggtccaag 240
tggtataatg attatgcagt atctgtgaaa agtcgaataa ccatcaaccc agacacatcc 300
aagaaccagt tctccctgca gctgaactct gtgactcccg aggacacggc tgtgtattac 360
tgtgcaagag ggaagggtgg taagaagggt ggtgcttttg atatctgggg ccaagggaca 420
atggtcaccg tctcttcagg aggtggcggg tctggtggag gcggtagcgg cggtggcgga 480
tcctcttctg agctgactca ggaccctgct gtgtctgtgg ccttgggaca gacagtcagg 540
atcacatgcc aaggagacag cctcagaagc tattatgcaa gctggtacca gcagaagcca 600
ggacaggctc ctgtacttgt catctatggt aaaaacaacc ggccctcagg gatcccagac 660
cgattctctg gctcctcctc aggcaacaca gcttccttga ccatcactgg ggctcaggcg 720
gaagatgagg ctgaatatta ctgtagctcc agcactcgta atcatgtgtt cttcggcaga 780
gggaccaagg tcaccgtcct cggtgcggcc gcaactacca cccctgcccc tcggccgccg 840
actccggccc caaccatcgc aagccaaccc ctctccttgc gccccgaagc ttgccgcccg 900
gccgcgggtg gagccgtgca tacccggggg ctggactttg cctgcgatat ctacatttgg 960
gccccgctgg ccggcacttg cggcgtgctc ctgctgtcgc tggtcatcac cctttactgc 1020
aagaggggcc ggaagaagct gctttacatc ttcaagcagc cgttcatgcg gcccgtgcag 1080
acgactcagg aagaggacgg atgctcgtgc agattccctg aggaggaaga gggggggatgc 1140

-continued

```
gaactgcgcg tcaagttctc acggtccgcc gacgcccccg catatcaaca gggccagaat   1200

cagctctaca acgagctgaa cctgggaagg agagaggagt acgacgtgct ggacaagcga   1260

cgcggacgcg acccggagat ggggggaaa ccacggcgga aaaaccctca ggaaggactg   1320

tacaacgaac tccagaaaga caagatggcg gaagcctact cagaaatcgg gatgaaggga   1380

gagcggagga ggggaaaggg tcacgacggg ctgtaccagg gactgagcac cgccactaag   1440

gatacctacg atgccttgca tatgcaagca ctcccacccc gg                      1482


<210> SEQ ID NO 12
<211> LENGTH: 494
<212> TYPE: PRT
<213> ORGANISM: Artificial Sequence
<220> FEATURE:
<223> OTHER INFORMATION: pLTG1901 EF1a MH1P--CD8TM-4-1BB-CD3 zeta

<400> SEQUENCE: 12

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Arg Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Gly Lys Gly Gly Lys
        115                 120                 125

Lys Gly Gly Ala Phe Asp Ile Trp Gly Gln Gly Thr Met Val Thr Val
    130                 135                 140

Ser Ser Gly Gly Gly Gly Ser Gly Gly Gly Gly Ser Gly Gly Gly Gly
145                 150                 155                 160

Ser Ser Ser Glu Leu Thr Gln Asp Pro Ala Val Ser Val Ala Leu Gly
                165                 170                 175

Gln Thr Val Arg Ile Thr Cys Gln Gly Asp Ser Leu Arg Ser Tyr Tyr
            180                 185                 190

Ala Ser Trp Tyr Gln Gln Lys Pro Gly Gln Ala Pro Val Leu Val Ile
        195                 200                 205

Tyr Gly Lys Asn Asn Arg Pro Ser Gly Ile Pro Asp Arg Phe Ser Gly
    210                 215                 220

Ser Ser Ser Gly Asn Thr Ala Ser Leu Thr Ile Thr Gly Ala Gln Ala
225                 230                 235                 240

Glu Asp Glu Ala Glu Tyr Tyr Cys Ser Ser Ser Thr Arg Asn His Val
                245                 250                 255

Phe Phe Gly Arg Gly Thr Lys Val Thr Val Leu Gly Ala Ala Ala Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300
```

-continued

```
Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

<210> SEQ ID NO 13
<211> LENGTH: 1479
<212> TYPE: DNA
<213> ORGANISM: Artificial Sequence
<220> FEATURE:
<223> OTHER INFORMATION: pLTG1902 Ef1a MH2P CD8TM-4-1BB-CD3 zeta

<400> SEQUENCE: 13

```
atgctgctgc tggtgaccag cctgctgctg tgcgaactgc cgcatccggc gtttctgctg      60

attccggagg tgcagctggt gcagtctggg ggaggcttgg tacagcctgg caggtcccag     120

agactctcct gtgcagcctc tggattcacc tttgatgatt atgccatgca ctgggtccgg     180

caagctccag ggaagggcct ggagtgggtc tcaggtatta gttggaatag tggtagcata     240

ggctatgcgg actctgtgaa gggccgattc accatctcca gagacaacgc caagaactcc     300

ctgtatctgc aaatgaacag tctgagagct gaggacacgg ccttgtatta ctgtgcaaaa     360

gatatttcgt cgtcagctgg taacgctttt gatatctggg gccaagggac aatggtcacc     420

gtctcttcag gaggtggcgg gtctggtgga ggcggtagcg gcggtggcgg atcctcttct     480

gagctgactc aggaccctgc tgtgtctgtg gccttgggac agacagtcag gatcacatgc     540

caaggagaca gactcagaag ctattatgca agctggtacc agcagaagcc aggacaggcc     600

cctgtacttg tcatctatgg taaaaacaac cggccctcag ggatcccaga ccgcttctct     660

ggctccgact caggagacac agcttccttg accatcactg gggctcaggc ggaagatgag     720

gctgactatt actgtcactc ccgtgacagt ggtggtaacc atgtggtatt cggcggaggc     780

acccagctga ccgtcctcgg tgcggccgca actaccaccc ctgcccctcg gccgccgact     840

ccggccccaa ccatcgcaag ccaacccctc tccttgcgcc ccgaagcttg ccgcccggcc     900

gcgggtggag ccgtgcatac ccgggggctg gactttgcct gcgatatcta catttgggcc     960

ccgctggccg gcacttgcgg cgtgctcctg ctgtcgctgg tcatcaccct ttactgcaag    1020
```

-continued aggggccgga agaagctgct ttacatcttc aagcagccgt tcatgcggcc cgtgcagacg 1080
actcaggaag aggacggatg ctcgtgcaga ttccctgagg aggaagaggg gggatgcgaa 1140
ctgcgcgtca agttctcacg gtccgccgac gcccccgcat atcaacaggg ccagaatcag 1200
ctctacaacg agctgaacct gggaaggaga gaggagtacg acgtgctgga caagcgacgc 1260
ggacgcgacc cggagatggg ggggaaacca cggcggaaaa accctcagga aggactgtac 1320
aacgaactcc agaaagacaa gatggcggaa gcctactcag aaatcgggat gaagggagag 1380
cggaggaggg gaaagggtca cgacgggctg taccagggac tgagcaccgc cactaaggat 1440
acctacgatg ccttgcatat gcaagcactc ccaccccgg 1479

<210> SEQ ID NO 14
<211> LENGTH: 493
<212> TYPE: PRT
<213> ORGANISM: Artificial Sequence
<220> FEATURE:
<223> OTHER INFORMATION: pLTG1902 Ef1a MH2P CD8TM-4-1BB-CD3 zeta

<400> SEQUENCE: 14

Met Leu Leu Leu Val Thr Ser Leu Leu Leu Cys Glu Leu Pro His Pro
1 5 10 15

Ala Phe Leu Leu Ile Pro Glu Val Gln Leu Val Gln Ser Gly Gly Gly
20 25 30

Leu Val Gln Pro Gly Arg Ser Gln Arg Leu Ser Cys Ala Ala Ser Gly
35 40 45

Phe Thr Phe Asp Asp Tyr Ala Met His Trp Val Arg Gln Ala Pro Gly
50 55 60

Lys Gly Leu Glu Trp Val Ser Gly Ile Ser Trp Asn Ser Gly Ser Ile
65 70 75 80

Gly Tyr Ala Asp Ser Val Lys Gly Arg Phe Thr Ile Ser Arg Asp Asn
85 90 95

Ala Lys Asn Ser Leu Tyr Leu Gln Met Asn Ser Leu Arg Ala Glu Asp
100 105 110

Thr Ala Leu Tyr Tyr Cys Ala Lys Asp Ile Ser Ser Ser Ala Gly Asn
115 120 125

Ala Phe Asp Ile Trp Gly Gln Gly Thr Met Val Thr Val Ser Ser Gly
130 135 140

Gly Gly Gly Ser Gly Gly Gly Gly Ser Gly Gly Gly Gly Ser Ser Ser
145 150 155 160

Glu Leu Thr Gln Asp Pro Ala Val Ser Val Ala Leu Gly Gln Thr Val
165 170 175

Arg Ile Thr Cys Gln Gly Asp Arg Leu Arg Ser Tyr Tyr Ala Ser Trp
180 185 190

Tyr Gln Gln Lys Pro Gly Gln Ala Pro Val Leu Val Ile Tyr Gly Lys
195 200 205

Asn Asn Arg Pro Ser Gly Ile Pro Asp Arg Phe Ser Gly Ser Asp Ser
210 215 220

Gly Asp Thr Ala Ser Leu Thr Ile Thr Gly Ala Gln Ala Glu Asp Glu
225 230 235 240

Ala Asp Tyr Tyr Cys His Ser Arg Asp Ser Gly Gly Asn His Val Val
245 250 255

Phe Gly Gly Gly Thr Gln Leu Thr Val Leu Gly Ala Ala Ala Thr Thr
260 265 270

Thr Pro Ala Pro Arg Pro Pro Thr Pro Ala Pro Thr Ile Ala Ser Gln

-continued

```
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490


<210> SEQ ID NO 15
<211> LENGTH: 1476
<212> TYPE: DNA
<213> ORGANISM: Artificial Sequence
<220> FEATURE:
<223> OTHER INFORMATION: pLTG1903 Ef1a MH6P CD8TM-4-1BB-CD3 zeta

<400> SEQUENCE: 15

atgctgctgc tggtgaccag cctgctgctg tgcgaactgc cgcatccggc gtttctgctg      60

attccgcagg tccagctggt gcagtctggg gctgaggtga agaagcctgg ggcctcagtg     120

aaggtctcct gcaaggcttc tggatacacc ttcaccggct actatatgca ctgggtgcga     180

caggcccctg gacaagggct tgagtggatg ggacggatca accctaacag tggtggcaca     240

aactatgcac agaagtttca gggcagggtc accatgacca ggaacacgtc catcagcaca     300

gcctacatgg agctgagcag gctgagatct gacgacacgg ccgtgtatta ctgtgcgaga     360

tccggctact actacggttt ggacgtctgg ggccaaggga ccacggtcac cgtctcctca     420

ggaggtggcg ggtctggtgg aggcggtagc ggcggtggcg gatcccagtc tgtgttgacg     480

cagccgccct cagcgtctgg gacccccggg cagcgggtca ccatctcttg ttctggaagt     540

cgctccaaca tcggaagaaa cactgtcaac tggtatcaac aactcccagg actggccccc     600

aaactcatca tccagaggag tgatcagcgg ccctcagggg tccctgaccg attctctggc     660

tccaagtctg tcacctcagc ctccctggcc atcagtgggc tccggtccga ggatgaggct     720

gattattact gcggaacatg ggataacagc ctgagtgctt atgtcttcgg aactgggacc     780

aagctgaccg tcctcggtgc ggccgcaact accacccctg cccctcggcc gccgactccg     840
```

```
gccccaacca tcgcaagcca acccctctcc ttgcgccccg aagcttgccg cccggccgcg    900

ggtggagccg tgcatacccg gggctggac tttgcctgcg atatctacat ttgggccccg     960

ctggccggca cttgcggcgt gctcctgctg tcgctggtca tcaccctta ctgcaagagg    1020

ggccggaaga agctgcttta catcttcaag cagccgttca tgcggcccgt gcagacgact   1080

caggaagagg acggatgctc gtgcagattc cctgaggagg aagagggggg atgcgaactg   1140

cgcgtcaagt tctcacggtc cgccgacgcc cccgcatatc aacagggcca gaatcagctc   1200

tacaacgagc tgaacctggg aaggagagag gagtacgacg tgctggacaa gcgacgcgga   1260

cgcgacccgg agatgggggg gaaaccacgg cggaaaaacc ctcaggaagg actgtacaac   1320

gaactccaga aagacaagat ggcggaagcc tactcagaaa tcgggatgaa gggagagcgg   1380

aggaggggaa agggtcacga cgggctgtac cagggactga gcaccgccac taaggatacc   1440

tacgatgcct tgcatatgca agcactccca ccccgg                             1476


<210> SEQ ID NO 16
<211> LENGTH: 492
<212> TYPE: PRT
<213> ORGANISM: Artificial Sequence
<220> FEATURE:
<223> OTHER INFORMATION: pLTG1903 Ef1a MH6P CD8TM-4-1BB-CD3 zeta

<400> SEQUENCE: 16

Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr Tyr Met His Trp Val Arg Gln Ala Pro Gly
    50                  55                  60

Gln Gly Leu Glu Trp Met Gly Arg Ile Asn Pro Asn Ser Gly Gly Thr
65                  70                  75                  80

Asn Tyr Ala Gln Lys Phe Gln Gly Arg Val Thr Met Thr Arg Asn Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Ser Gly Tyr Tyr Tyr Gly Leu Asp
        115                 120                 125

Val Trp Gly Gln Gly Thr Thr Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Ala Ser Gly Thr Pro Gly Gln Arg Val Thr Ile Ser
                165                 170                 175

Cys Ser Gly Ser Arg Ser Asn Ile Gly Arg Asn Thr Val Asn Trp Tyr
            180                 185                 190

Gln Gln Leu Pro Gly Leu Ala Pro Lys Leu Ile Ile Gln Arg Ser Asp
        195                 200                 205

Gln Arg Pro Ser Gly Val Pro Asp Arg Phe Ser Gly Ser Lys Ser Val
    210                 215                 220

Thr Ser Ala Ser Leu Ala Ile Ser Gly Leu Arg Ser Glu Asp Glu Ala
225                 230                 235                 240

Asp Tyr Tyr Cys Gly Thr Trp Asp Asn Ser Leu Ser Ala Tyr Val Phe
                245                 250                 255
```

```
Gly Thr Gly Thr Lys Leu Thr Val Leu Gly Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490


<210> SEQ ID NO 17
<211> LENGTH: 1476
<212> TYPE: DNA
<213> ORGANISM: Artificial Sequence
<220> FEATURE:
<223> OTHER INFORMATION: pLTG1904 Ef1a M1-4S CD8TM-4-1BB-CD3 zeta

<400> SEQUENCE: 17

atgctgctgc tggtgaccag cctgctgctg tgcgaactgc cgcatccggc gtttctgctg      60

attccggagg tccagctggt acagtctggg ggaggcttgg tacagcctgg ggggtccctg     120

agactctcct gtgcagcctc tggattcacc tttgatgatt atgccatgca ctgggtccgg     180

caagctccag ggaagggcct ggagtgggtc tcaggtatta gttggaatag tggtagcata     240

ggctatgcgg actctgtgaa gggccgattc accatctcca gagacaacgc caagaactcc     300

ctgtatctgc aaatgaacag tctgagagct gaggacacgg ccttgtatta ctgtgcaaaa     360

gatttatcgt cagtggctgg accctttaac tactggggcc agggcaccct ggtcaccgtc     420

tcctcaggag gtggcgggtc tggtggaggc ggtagcggcg gtggcggatc ctcttctgag     480

ctgactcagg accctgctgt gtctgtggcc ttgggacaga cagtcaggat cacatgccaa     540

ggagacagcc tcagaagcta ttatgcaagc tggtaccagc agaagccagg acaggcccct     600

gtacttgtca tctatggtaa aaacaaccgg ccctcaggga tcccagaccg attctctggc     660

tccagctcag gaaacacagc ttccttgacc atcactgggg ctcaggcgga ggatgaggct     720
```

```
gactattact gtaactcccg ggacagcagt ggtaaccatc tggtattcgg cggaggcacc    780

cagctgaccg tcctcggtgc ggccgcaact accaccccctg cccctcggcc gccgactccg    840

gccccaacca tcgcaagcca acccctctcc ttgcgccccg aagcttgccg cccggccgcg    900

ggtggagccg tgcatacccg gggctggac tttgcctgcg atatctacat ttgggccccg    960

ctggccggca cttgcggcgt gctcctgctg tcgctggtca tcacccttta ctgcaagagg   1020

ggccggaaga agctgcttta catcttcaag cagccgttca tgcggcccgt gcagacgact   1080

caggaagagg acggatgctc gtgcagattc cctgaggagg aagaggggg atgcgaactg   1140

cgcgtcaagt tctcacggtc cgccgacgcc cccgcatatc aacagggcca gaatcagctc   1200

tacaacgagc tgaacctggg aaggagagag gagtacgacg tgctggacaa gcgacgcgga   1260

cgcgacccgg agatggggg gaaaccacgg cggaaaaacc ctcaggaagg actgtacaac   1320

gaactccaga aagacaagat ggcggaagcc tactcagaaa tcgggatgaa gggagagcgg   1380

aggaggggaa agggtcacga cgggctgtac cagggactga gcaccgccac taaggatacc   1440

tacgatgcct tgcatatgca agcactccca ccccgg                             1476
```

```
<210> SEQ ID NO 18
<211> LENGTH: 492
<212> TYPE: PRT
<213> ORGANISM: Artificial Sequence
<220> FEATURE:
<223> OTHER INFORMATION: pLTG1904 Ef1a M1-4S CD8TM-4-1BB-CD3 zeta

<400> SEQUENCE: 18

Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Gly Gly
            20                  25                  30

Leu Val Gln Pro Gly Gly Ser Leu Arg Leu Ser Cys Ala Ala Ser Gly
        35                  40                  45

Phe Thr Phe Asp Asp Tyr Ala Met His Trp Val Arg Gln Ala Pro Gly
    50                  55                  60

Lys Gly Leu Glu Trp Val Ser Gly Ile Ser Trp Asn Ser Gly Ser Ile
65                  70                  75                  80

Gly Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Leu Tyr Tyr Cys Ala Lys Asp Leu Ser Ser Val Ala Gly Pro
        115                 120                 125

Phe Asn Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Ser Ser Glu
145                 150                 155                 160

Leu Thr Gln Asp Pro Ala Val Ser Val Ala Leu Gly Gln Thr Val Arg
                165                 170                 175

Ile Thr Cys Gln Gly Asp Ser Leu Arg Ser Tyr Tyr Ala Ser Trp Tyr
            180                 185                 190

Gln Gln Lys Pro Gly Gln Ala Pro Val Leu Val Ile Tyr Gly Lys Asn
        195                 200                 205

Asn Arg Pro Ser Gly Ile Pro Asp Arg Phe Ser Gly Ser Ser Ser Gly
    210                 215                 220
```

-continued

```
Asn Thr Ala Ser Leu Thr Ile Thr Gly Ala Gln Ala Glu Asp Glu Ala
225                 230                 235                 240

Asp Tyr Tyr Cys Asn Ser Arg Asp Ser Ser Gly Asn His Leu Val Phe
                245                 250                 255

Gly Gly Gly Thr Gln Leu Thr Val Leu Gly Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 19
<211> LENGTH: 72
<212> TYPE: DNA
<213> ORGANISM: Homo sapiens

<400> SEQUENCE: 19

```
atctacatct gggcgccctt ggccgggact tgtggggtcc ttctcctgtc actggttatc     60

accctttact gc                                                         72
```

<210> SEQ ID NO 20
<211> LENGTH: 22
<212> TYPE: PRT
<213> ORGANISM: Homo sapiens

<400> SEQUENCE: 20

```
Ile Trp Ala Pro Leu Ala Gly Thr Cys Gly Val Leu Leu Leu Ser Leu
1               5                   10                  15

Val Ile Thr Leu Tyr Cys
            20
```

<210> SEQ ID NO 21

<211> LENGTH: 135
<212> TYPE: DNA
<213> ORGANISM: Homo sapiens

<400> SEQUENCE: 21
accacgacgc cagcgccgcg accaccaaca ccggcgccca ccatcgcgtc gcagcccctg 60
tccctgcgcc cagaggcgtg ccggccagcg gcggggggcg cagtgcacac gagggggctg 120
gacttcgcct gtgat 135

<210> SEQ ID NO 22
<211> LENGTH: 47
<212> TYPE: PRT
<213> ORGANISM: Homo sapiens

<400> SEQUENCE: 22

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp Ile Tyr
35 40 45

<210> SEQ ID NO 23
<211> LENGTH: 42
<212> TYPE: PRT
<213> ORGANISM: Artificial Sequence
<220> FEATURE:
<223> OTHER INFORMATION: hinge region of CD8.alpha

<400> SEQUENCE: 23

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 24
<211> LENGTH: 106
<212> TYPE: PRT
<213> ORGANISM: Homo sapiens

<400> SEQUENCE: 24

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Ser Ser Pro
35 40 45

Val Lys Ala Gly Val Glu Thr Thr Thr Pro Ser Lys Gln Ser Asn Asn
50 55 60

Lys Tyr Ala Ala Ser Ser Tyr Leu Ser Leu Thr Pro Glu Gln Trp Lys
65 70 75 80

Ser His Arg Ser Tyr Ser Cys Gln Val Thr His Glu Gly Ser Thr Val
85 90 95

Glu Lys Thr Val Ala Pro Thr Glu Cys Ser
100 105

<210> SEQ ID NO 25

-continued

```
<211> LENGTH: 126
<212> TYPE: DNA
<213> ORGANISM: Homo sapiens

<400> SEQUENCE: 25

aaacggggca gaaagaaact cctgtatata ttcaaacaac catttatgag accagtacaa     60

actactcaag aggaagatgg ctgtagctgc cgatttccag aagaagaaga aggaggatgt    120

gaactg                                                               126


<210> SEQ ID NO 26
<211> LENGTH: 42
<212> TYPE: PRT
<213> ORGANISM: Homo sapiens

<400> SEQUENCE: 26

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 27
<211> LENGTH: 336
<212> TYPE: DNA
<213> ORGANISM: Homo sapiens

<400> SEQUENCE: 27

agagtgaagt tcagcaggag cgcagacgcc cccgcgtaca agcagggcca gaaccagctc     60

tataacgagc tcaatctagg acgaagagag gagtacgatg ttttggacaa gagacgtggc    120

cgggaccctg agatgggggg aaagccgaga aggaagaacc ctcaggaagg cctgtacaat    180

gaactgcaga aagataagat ggcggaggcc tacagtgaga ttgggatgaa aggcgagcgc    240

cggaggggca aggggcacga tggcctttac cagggtctca gtacagccac caaggacacc    300

tacgacgccc ttcacatgca ggccctgccc cctcgc                              336


<210> SEQ ID NO 28
<211> LENGTH: 112
<212> TYPE: PRT
<213> ORGANISM: Homo sapiens

<400> SEQUENCE: 28

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

```
<210> SEQ ID NO 29
<211> LENGTH: 726
<212> TYPE: DNA
<213> ORGANISM: Artificial Sequence
<220> FEATURE:
<223> OTHER INFORMATION: Scvf cd 19

<400> SEQUENCE: 29

gacatccaga tgacacagac tacatcctcc ctgtctgcct ctctgggaga cagagtcacc      60

atcagttgca gggcaagtca ggacattagt aaatatttaa attggtatca gcagaaacca     120

gatggaactg ttaaactcct gatctaccat acatcaagat tacactcagg agtcccatca     180

aggttcagtg gcagtgggtc tggaacagat tattctctca ccattagcaa cctggagcaa     240

gaagatattg ccacttactt ttgccaacag ggtaatacgc ttccgtacac gttcggaggg     300

gggaccaagc tggagatcac aggtggcggt ggctcgggcg gtggtgggtc gggtggcggc     360

ggatctgagg tgaaactgca ggagtcagga cctggcctgg tggcgccctc acagagcctg     420

tccgtcacat gcactgtctc aggggtctca ttacccgact atggtgtaag ctggattcgc     480

cagcctccac gaaagggtct ggagtggctg ggagtaatat ggggtagtga aaccacatac     540

tataattcag ctctcaaatc cagactgacc atcatcaagg acaactccaa gagccaagtt     600

ttcttaaaaa tgaacagtct gcaaactgat gacacagcca tttactactg tgccaaacat     660

tattactacg gtggtagcta tgctatggac tactggggcc aaggaacctc agtcaccgtc     720

tcctca                                                                726


<210> SEQ ID NO 30
<211> LENGTH: 242
<212> TYPE: PRT
<213> ORGANISM: Artificial Sequence
<220> FEATURE:
<223> OTHER INFORMATION: Scvf cd 19

<400> SEQUENCE: 30

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
```

-continued

```
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser
```